US009820757B2

(12) United States Patent
Victor

(10) Patent No.: US 9,820,757 B2
(45) Date of Patent: Nov. 21, 2017

(54) INSTRUMENT FOR RESHAPING THE HEAD OF A FEMUR

(71) Applicant: Greatbatch Ltd., Clarence, NY (US)

(72) Inventor: Gary C. Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 694 days.

(21) Appl. No.: 14/252,572

(22) Filed: Apr. 14, 2014

(65) Prior Publication Data
US 2014/0309642 A1    Oct. 16, 2014

Related U.S. Application Data

(60) Provisional application No. 61/811,453, filed on Apr. 12, 2013.

(51) Int. Cl.
*A61B 17/16* (2006.01)

(52) U.S. Cl.
CPC .............................. *A61B 17/1668* (2013.01)

(58) Field of Classification Search
CPC . A61B 17/16; A61B 17/1613–17/1633; A61B 17/164–17/1646; A61B 17/1655–17/1659; A61B 17/1662; A61B 17/1684; A61B 17/1695; A61B 2017/1602; A61B 2017/1648–2017/1653; A61B 17/1668; A01G 23/067; B27C 3/00; B27C 3/02; B27C 3/06; B27G 15/00; B27G 15/02
USPC ............................... 606/80, 84; 408/204, 206
See application file for complete search history.

(56) References Cited

U.S. PATENT DOCUMENTS

| | | | | |
|---|---|---|---|---|
| 91,225 A | * | 6/1869 | Cutler | B23B 51/05 408/186 |
| 2,618,991 A | * | 11/1952 | Charles | B23B 51/05 125/20 |
| 2,803,153 A | * | 8/1957 | Golbeck | B23B 51/05 408/174 |
| 2,853,904 A | * | 9/1958 | Mackey | B23B 51/0473 408/206 |
| 3,055,443 A | * | 9/1962 | Edwards | E21B 10/04 175/333 |
| 3,610,768 A | | 10/1971 | Cochran | |
| 3,667,456 A | * | 6/1972 | Charnley | A61B 17/1668 606/81 |
| 3,771,895 A | * | 11/1973 | Meyer | B23B 51/05 408/157 |
| 3,880,546 A | | 4/1975 | Segal | |
| 4,072,437 A | * | 2/1978 | Smith | B23C 5/22 407/118 |

(Continued)

FOREIGN PATENT DOCUMENTS

DE WO 2004094842 A1 * 11/2004 ............ E04B 1/585

OTHER PUBLICATIONS

Derek McMinn, Birmingham Hip Resurfacing System, Smith & Nephew, Jan. 2007.

*Primary Examiner* — Eric S Gibson
(74) *Attorney, Agent, or Firm* — Steven W. Winn

(57) ABSTRACT

An orthopedic cutting tool for reshaping the end of a femur is described. The cutting tool comprises three separate cutting blades that are positioned within different locations within a housing to reshape the end of the femur to thus receive a femur head prosthetic. The cutting tool forms the reshaped femur end in one cutting motion.

26 Claims, 20 Drawing Sheets

(56) References Cited

U.S. PATENT DOCUMENTS

| | | | |
|---|---|---|---|
| 4,078,622 A * | 3/1978 | Taylor-Myers | B24D 7/06 125/20 |
| 4,147,464 A * | 4/1979 | Watson | B23B 51/05 408/206 |
| 4,284,080 A * | 8/1981 | Rehder | A61B 17/1668 606/53 |
| 4,295,763 A * | 10/1981 | Cunniff | B23B 51/05 144/24 |
| 4,637,442 A | 1/1987 | Mozer | |
| 5,015,128 A * | 5/1991 | Ross, Jr. | B23B 51/0413 175/405.1 |
| 5,203,653 A | 4/1993 | Kudla | |
| 5,218,888 A * | 6/1993 | Merrill | B23B 51/0406 408/204 |
| 5,451,128 A * | 9/1995 | Hattersley | B23B 51/0466 407/107 |
| 5,791,424 A * | 8/1998 | Moser | B28D 1/041 175/394 |
| 5,895,178 A * | 4/1999 | Young | B23B 51/0426 144/21 |
| 5,976,144 A | 11/1999 | Fishbein et al. | |
| 6,007,279 A * | 12/1999 | Malone, Jr. | B23B 51/0433 144/150 |
| 6,152,661 A * | 11/2000 | Thrasher | B23B 51/0433 408/204 |
| 6,857,831 B2 * | 2/2005 | Davis | B23B 51/0433 408/204 |
| 7,097,397 B2 * | 8/2006 | Keightley | B23B 51/0473 408/204 |
| 7,837,686 B1 | 11/2010 | Tulkis | |
| 7,918,856 B2 * | 4/2011 | Guelat | A61B 17/1668 606/80 |
| 8,152,808 B2 | 4/2012 | Steiner et al. | |
| 8,152,855 B2 * | 4/2012 | Tulkis | A61B 17/1668 606/104 |
| 8,337,123 B2 | 12/2012 | Ishida | |
| 8,343,157 B2 | 1/2013 | Scott et al. | |
| 8,840,344 B2 * | 9/2014 | Stenman | B23B 51/05 408/186 |
| 2004/0179911 A1 * | 9/2004 | Keightley | B23B 31/11 408/204 |
| 2004/0193168 A1 | 9/2004 | Long et al. | |
| 2005/0251145 A1 * | 11/2005 | Desarzens | A61B 17/1668 606/80 |
| 2006/0015111 A1 * | 1/2006 | Fenton | A61B 17/1637 606/80 |
| 2007/0280798 A1 * | 12/2007 | Zeiler | B23B 51/0413 408/201 |
| 2007/0299451 A1 * | 12/2007 | Tulkis | A61B 17/175 606/79 |
| 2008/0183297 A1 * | 7/2008 | Boileau | A61F 2/4612 623/19.14 |
| 2008/0300600 A1 * | 12/2008 | Guelat | A61B 17/1668 606/80 |
| 2009/0208302 A1 * | 8/2009 | Durfee | B27G 15/00 408/206 |
| 2009/0209963 A1 * | 8/2009 | Jamali | A61B 17/1635 606/81 |
| 2009/0326539 A1 * | 12/2009 | Neumeyer | A61B 17/1637 606/80 |
| 2010/0160916 A1 * | 6/2010 | Chana | A61B 17/1668 606/83 |
| 2011/0071526 A1 | 3/2011 | Lechot | |
| 2011/0118743 A1 * | 5/2011 | Cannell | A61B 17/1668 606/80 |
| 2011/0125155 A1 * | 5/2011 | Mutchler | A61B 17/1684 606/87 |
| 2011/0144649 A1 | 6/2011 | Victor et al. | |
| 2011/0182683 A1 * | 7/2011 | Miyanaga | B23B 51/0433 408/206 |
| 2011/0288554 A1 * | 11/2011 | Victor | A61B 17/1659 606/83 |
| 2011/0306980 A1 * | 12/2011 | Victor | A61B 17/1668 606/83 |
| 2012/0165832 A1 | 6/2012 | Oostman et al. | |
| 2014/0309642 A1 * | 10/2014 | Victor | A61B 17/1668 606/84 |
| 2015/0257769 A1 * | 9/2015 | Papenfuss | A61B 17/1617 606/80 |
| 2015/0257772 A1 * | 9/2015 | Papenfuss | A61B 17/1617 606/81 |

* cited by examiner

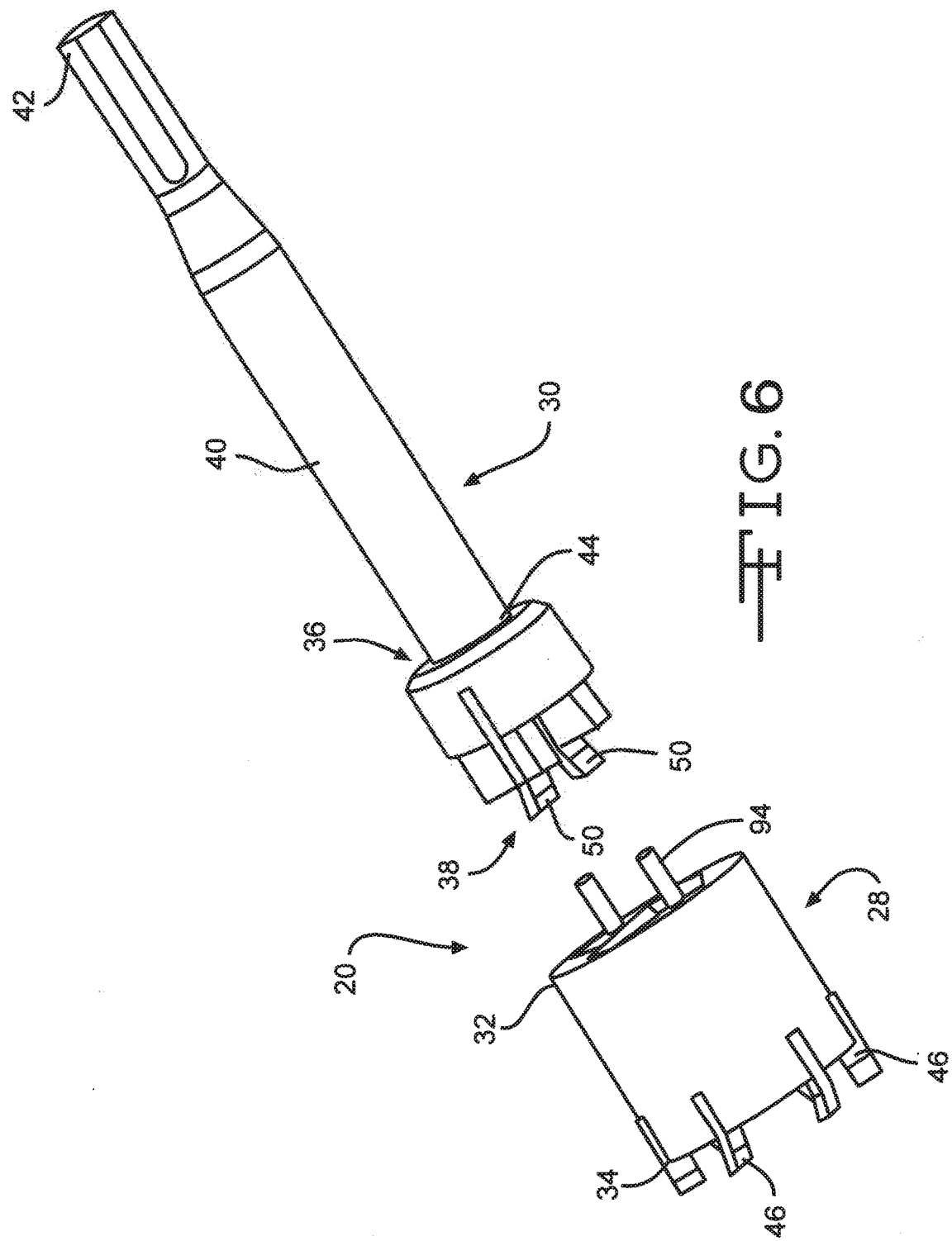

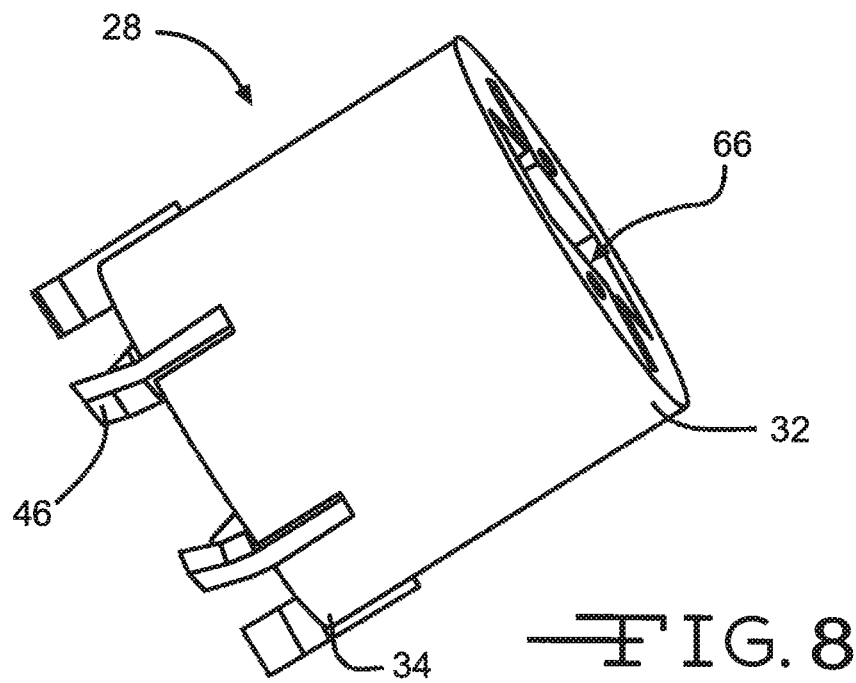
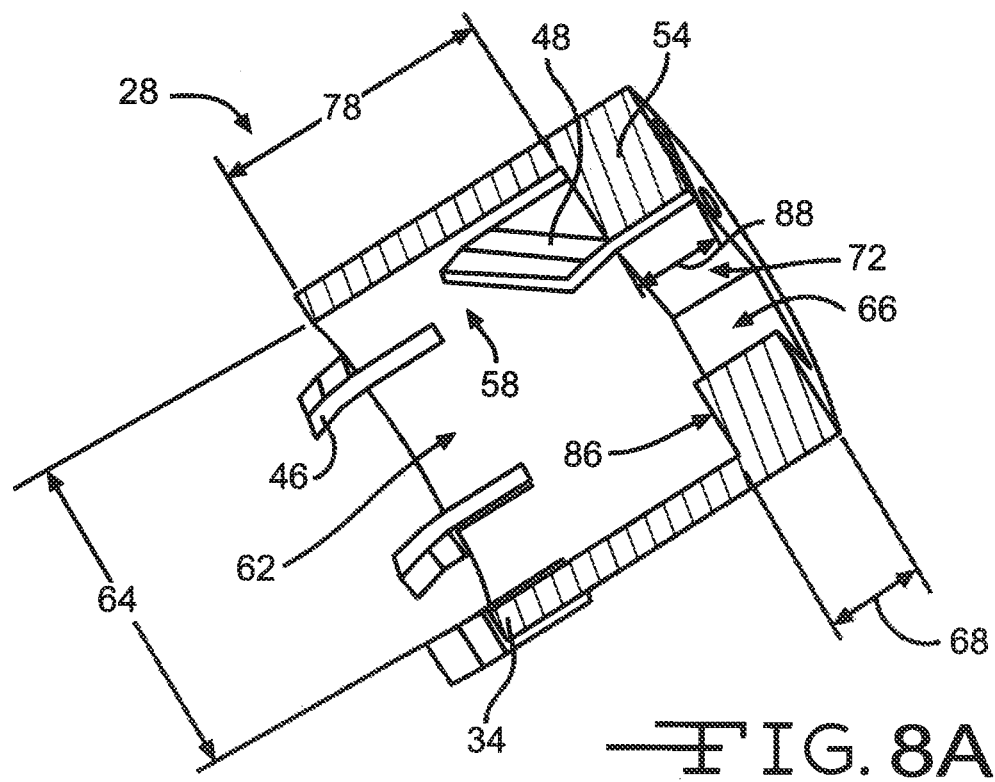

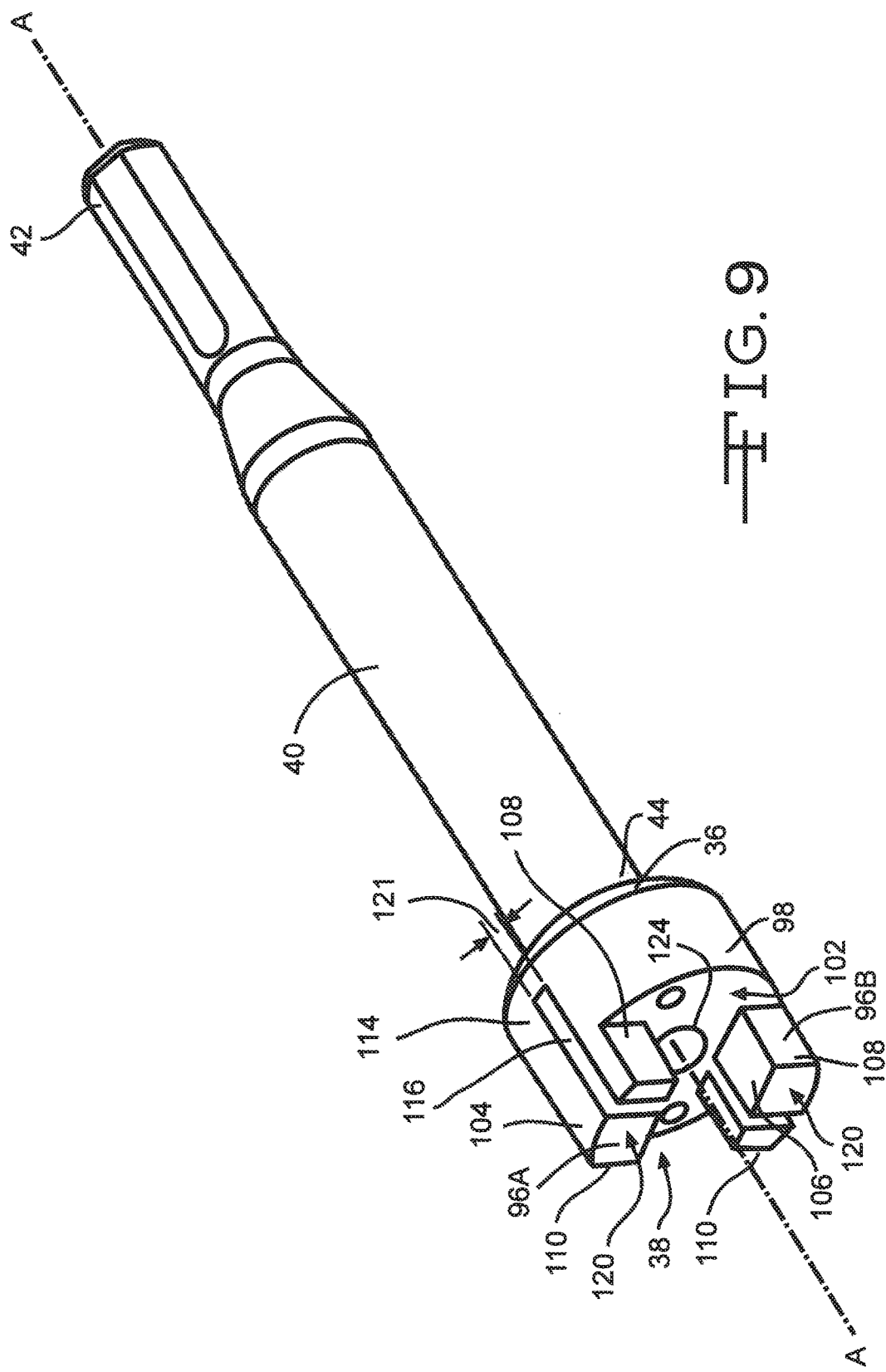

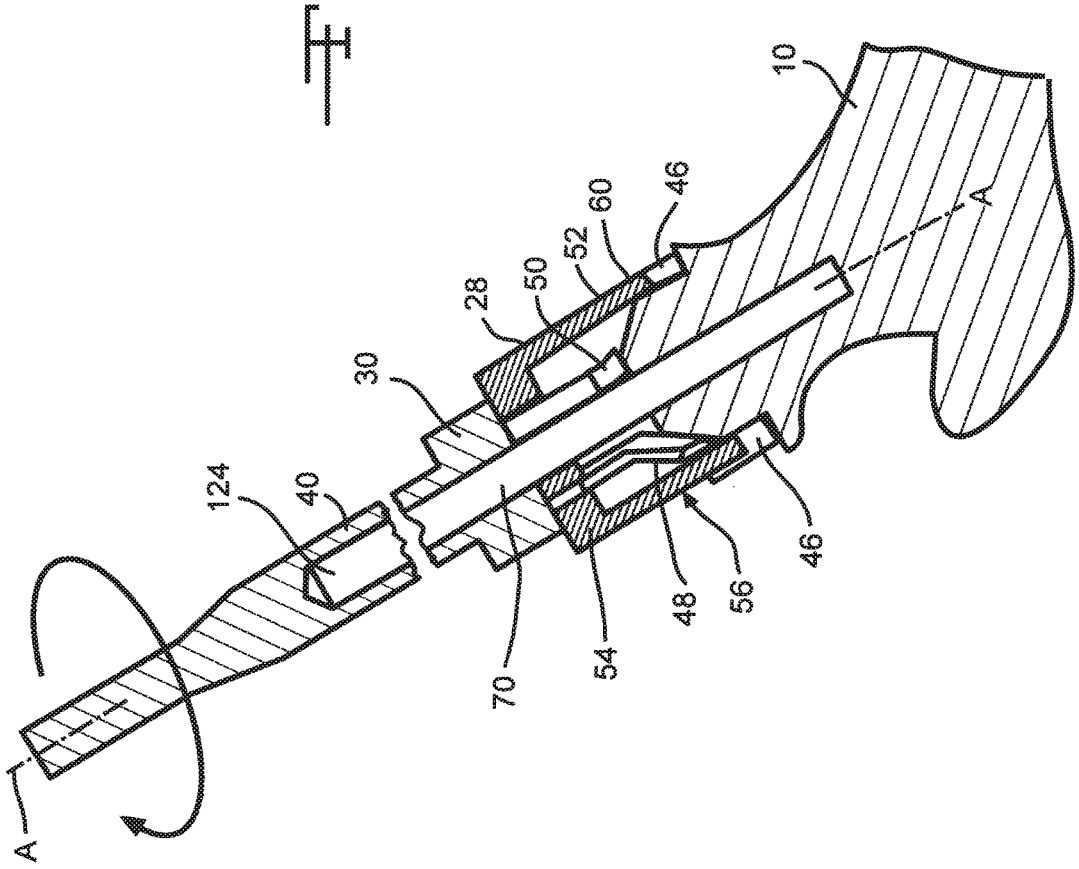

INSTRUMENT FOR RESHAPING THE HEAD OF A FEMUR

CROSS REFERENCE TO RELATED APPLICATION

This application claims priority to U.S. provisional application Ser. No. 61/811,453, filed Apr. 12, 2013.

FIELD OF THE INVENTION

The present invention relates to the art of orthopedic cutting devices, more particularly, to an orthopedic cutting device designed to remove bone and tissue from a femur.

BACKGROUND OF THE INVENTION

Hip arthroplasty involves removing a diseased hip joint and replacing it with an artificial joint. In one procedure, commonly referred to as a total hip replacement, the head of the femur is removed and a femoral stem having a femoral head prosthesis end is positioned within the end of the bone. The femoral head is received within a prosthetic cup positioned within the acetabulum. While it has been shown that total hip replacement surgery is effective for some patients, a total hip replacement surgical procedure may cause neuromuscular damage. Furthermore, removing the end of the femur may cause bleeding problems, infection, or other complications that are not desirable.

Therefore, an alternative hip replacement surgical procedure was developed in which the head of the femur is resurfaced, as opposed to being removed in a total hip replacement surgery, to receive a femoral head prosthetic.

Since the head of the femur is not removed, the femur resurfacing procedure may be better suited for some patients in which removal of the end of the femur may cause complications or restrict future mobility.

During a hip resurfacing procedure, the head of a femur 10 is reshaped to receive a femoral head prosthetic (not shown). Historically, the procedure utilizes three separate cutting tools to reshape the head of the femur 10 into a desired form as shown in FIG. 4. In a first step, a sleeve cutter 12, an example of which is illustrated in FIG. 1, is used to form a cylindrical shape at the head of the femur 10. After the cylindrical shape has been formed using the sleeve cutter 12, a plan cutter 14, an example of which is illustrated in FIG. 2, is used to create a planar surface at the proximal end of the femur 10. Finally, a chamfer cutter 16, an example of which is illustrated in FIG. 3, is used to impart a chamfered surface on the head of the femur 10. The resultant reshaped femur, shown in FIG. 4, is now ready to receive a femoral head prosthetic that is positioned over the end of the reshaped femur 10.

Use of the three separate cutters 12, 14, 16 during this bone reshaping procedure is not ideal. Each cutting tool requires proper positioning and alignment with respect to the bone 10 to ensure proper fit and function of the femoral head prosthesis. Utilization of three separate cutting tools creates an inherent risk that the tools might not be properly positioned and aligned with respect to the cut created by the prior tool. Therefore, there is a possibility that the head of the femur might not be properly shaped for proper positioning of the femoral head prosthetic. For example, these traditional cutting tools generally require the use of a handle to interface the cutting tool with a drive shaft that imparts rotation to the cutting blade. This interface between the handle and the cutting tool may not be secure. Therefore, because the handle may not be adequately positioned and secured to the cutting tool, the cutting surface of the tool may be askew from its proper position or the cutting surface may shift during use. Therefore, possible misalignment between the handle and the cutting instrument may result in an improperly shaped femur.

In addition, a slight misalignment in positioning the cutting surface of the cutting tool to the bone by the surgeon of any one of the three prior art cutting tools, could also result in an improperly shaped femur, thereby leading to poor positioning of the femoral head prosthesis. In either case, an improperly fit femoral head prosthesis may negatively affect patient mobility and also require that the patient undergo additional surgical procedures to correct the misalignment.

The cutting tool of the present invention addresses these deficiencies by providing a tool that is capable of reshaping the head of the femur in one cutting motion at one time. That is in contrast to using three separate tools of the prior art. According to the present invention, the desired form of the reshaped femur (FIG. 4) is obtained by incorporating different cutting blades into one tool. Therefore, the possibility of incorrectly reshaping the end of the femur as a result of misalignment of the cutting blades to the bone is reduced. As a result, the possibility of an improperly fit femoral head prosthesis is minimized and patient mobility is improved.

SUMMARY OF THE INVENTION

Thus, a new orthopedic cutting tool designed to cut and reshape the head of a femur to receive a femoral head prosthetic is provided. The cutting tool of the present invention comprises a housing in which three different cutting blades, namely a first or post forming blade, a second or chamfer blade, and a third or plan cutting blade, are positioned therewithin.

Specifically, the three different cutting blades of the present invention are securely received within two separate housing segments, a first housing segment and a second housing segment that are connected to each other. The first and second housing segments are positioned with respect to each other such that the three separate cutting blades are positioned at differing depths within the instrument to reshape the head of a femur into a desired cylindrical form.

The first housing segment is of a cylindrical form comprising an annular sidewall designed to be fit over the end of a bone. The first or post cutting blade is preferably positioned within the sidewall of the first housing segment. In a preferred embodiment, a plurality of first blades is positioned within the distal end of the sidewall of the first housing segment. Each of the first blades is bent at a rake angle so that when they are rotated, the cutting edges reshape the head of the femur into a cylindrical shape.

The second or chamfer cutting blade is also positioned within the first housing segment. The second blade extends outwardly from within the cavity formed by the annular sidewall of the first housing segment. The second blade is bent at a rake angle and a chamfer angle. The angular orientation of the cutting edge of the second blade, defined by its rake and chamfer angles, enables the second blade to form a chamfered surface at the distal end of the cylindrical post formed at the end of a bone.

The second housing segment resides proximate of the first housing segment along a longitudinal axis. The second housing segment comprises a platform that extends longitudinally from a second base. The first and second housing segments are preferably joined together in a keyed relationship in which the platform which extends from the distal end of the second housing segment is received within an opening of the first housing segment. The third blade is received and secured within a slot that extends through at least a portion of the platform of the second housing segment. The third blade is orientated to cut a planar surface at the proximal end of a femur.

Rotation of the cutting instrument of the present invention against a bone causes the end of the bone to be shaped into the desired multi-faceted form shown in FIG. 4. Thus, unlike the prior art, the femoral head is reshaped into a desired form in a single cutting motion at one time. Since all the cutting blades are incorporated into one tool, the possibility of causing prosthesis misalignment is reduced, thereby improving patient outcomes and patient mobility.

BRIEF DESCRIPTION OF THE DRAWINGS

FIG. 6 shows a perspective view of an embodiment of the housing segments that comprise the bone cutter of the present invention.

FIG. 8 illustrates an embodiment of the first housing segment in which a plurality of first cutting blades have been positioned therewithin.

FIG. 8A is a cross sectional view of an embodiment of the first housing segment in which the first and second cutting blades have been positioned therewithin.

FIGS. 9 and 9A illustrate an embodiment of the second housing segment of the bone cutter of the present invention.

FIG. 13 is a cross-sectional view of the bone cutter of the present invention cutting the end of a bone.

DETAILED DESCRIPTION OF THE PREFERRED EMBODIMENT

Figure 1:
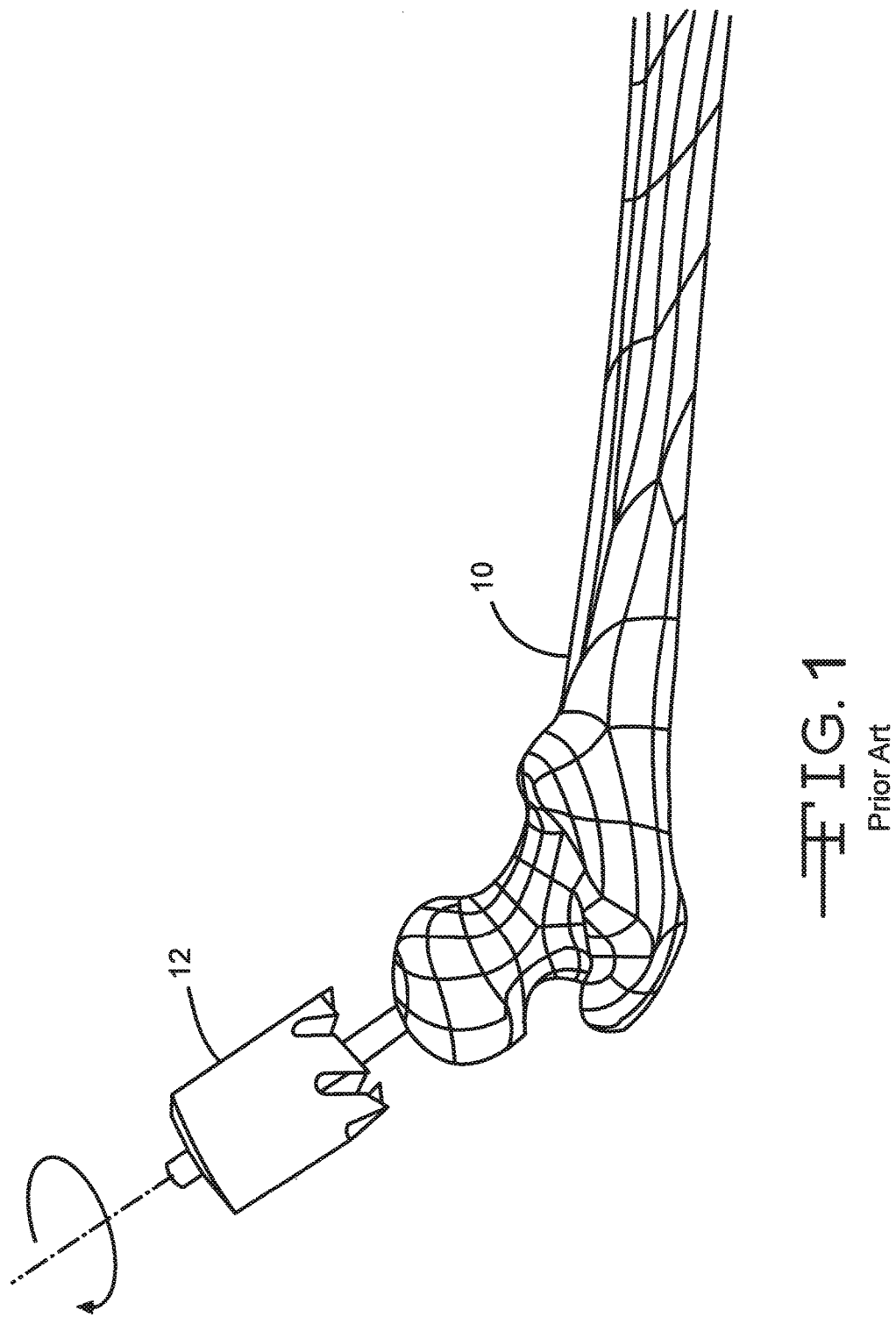
FIG. 1 is a perspective view of an embodiment of a prior art sleeve cutter 12 used to reshape the end of a bone.
Figure 2:
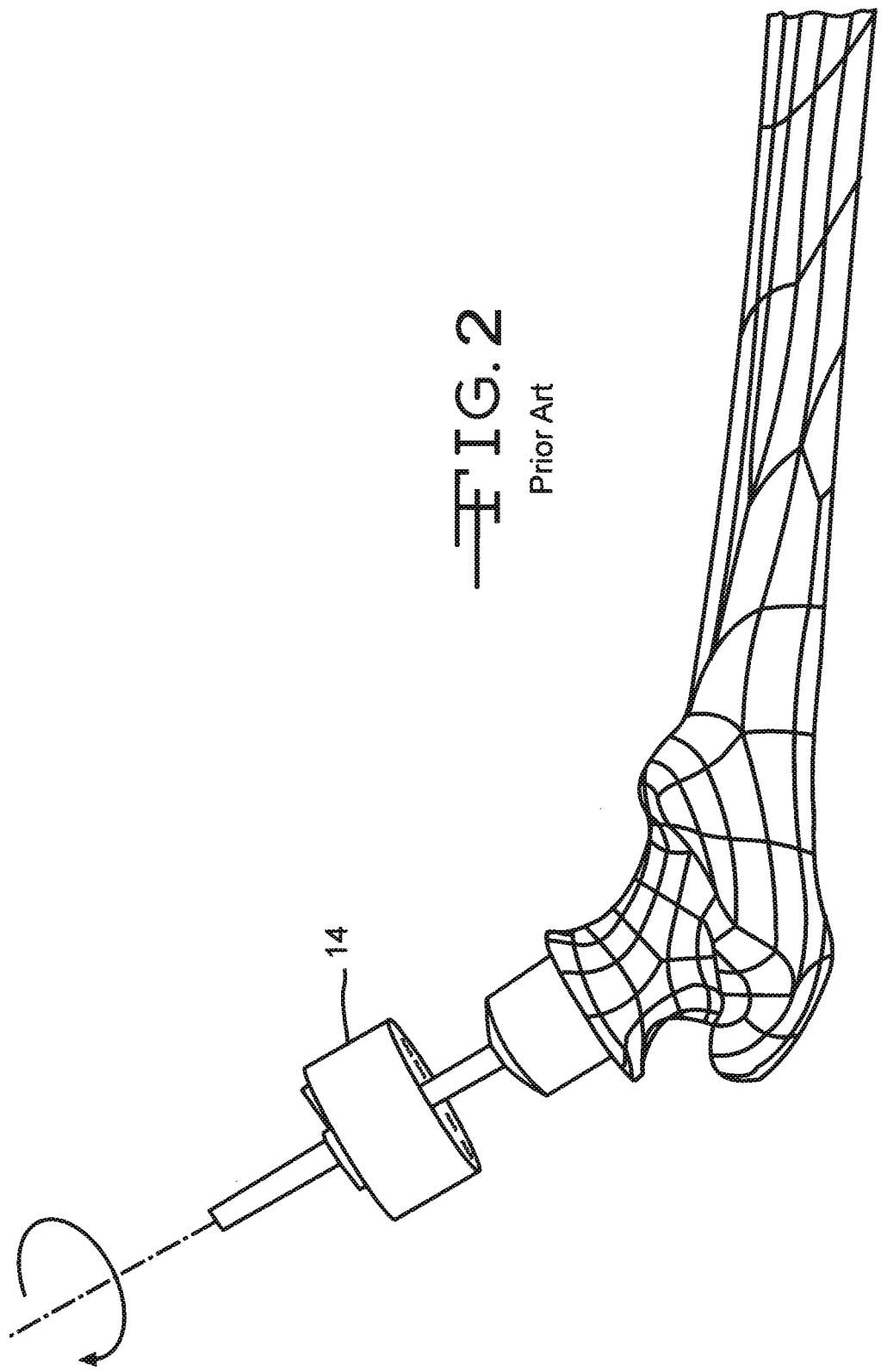
FIG. 2 is a perspective view of an embodiment of a prior art plan cutter 14 used to reshape the end of a bone.
Figure 3:
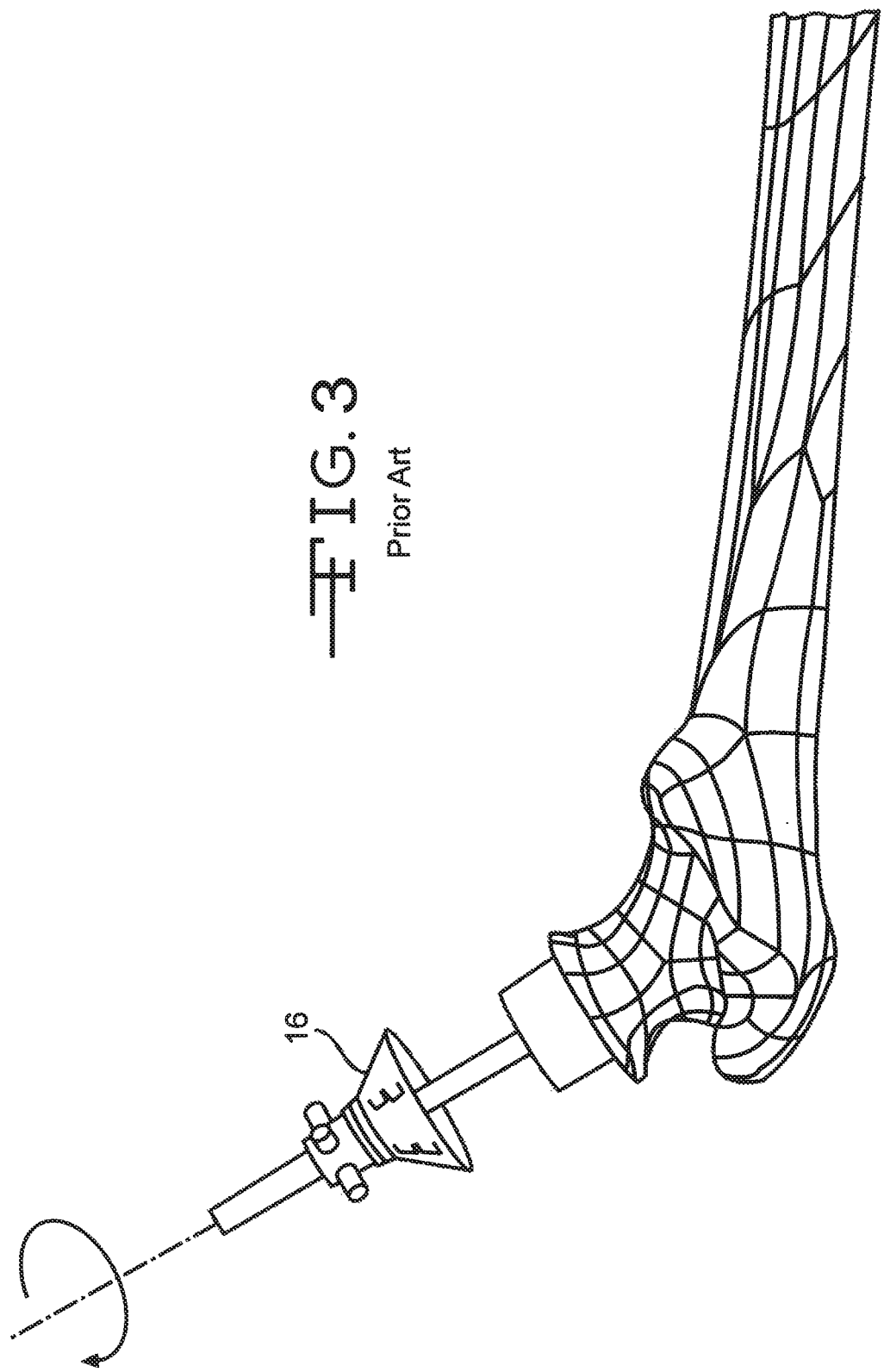
FIG. 3 is a perspective view of an embodiment of a prior art chamfer cutter 16 used to reshape the end of a bone.
Figure 4:
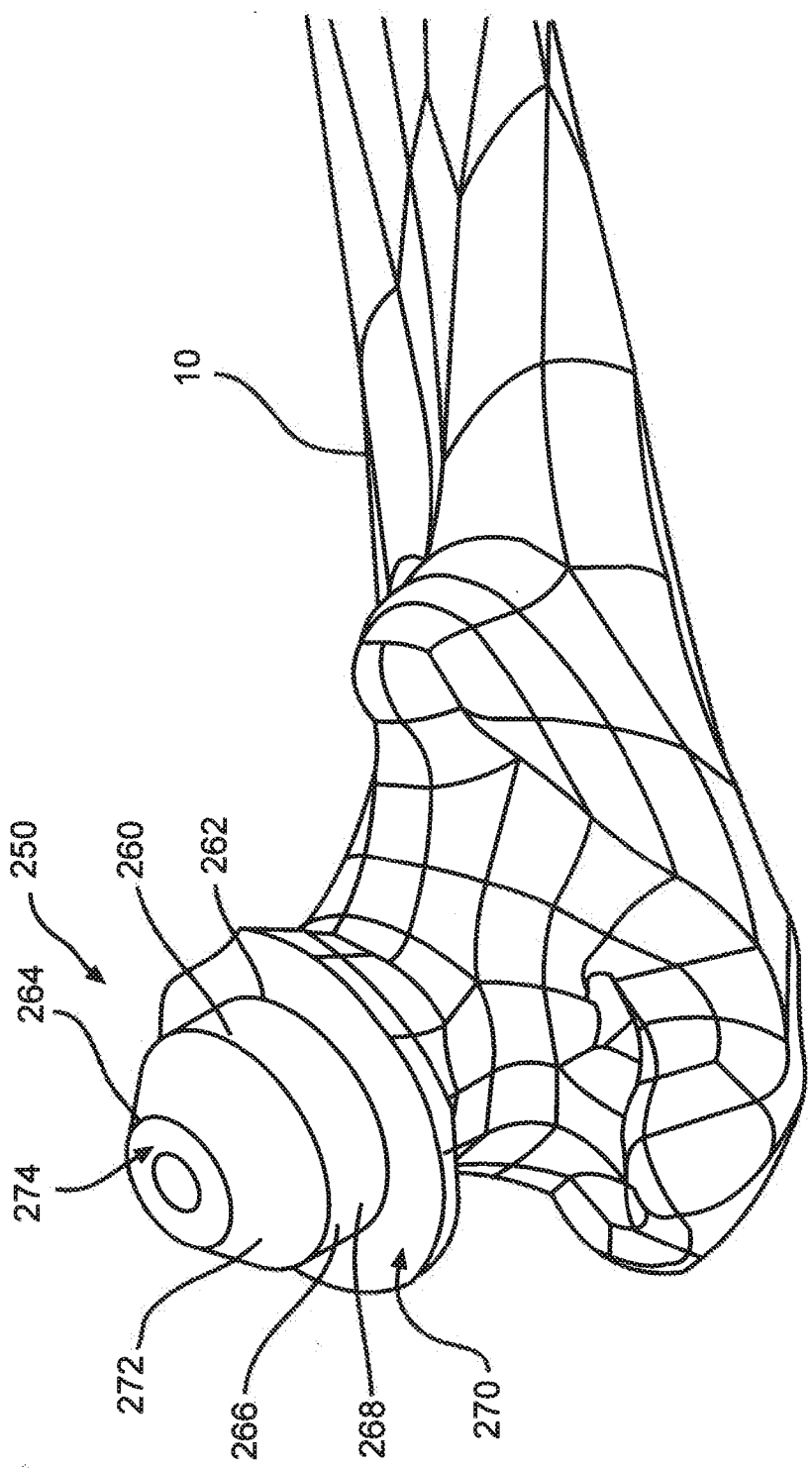
FIG. 4 illustrates a perspective view of the head of a femur having been reshaped to a desired form.

Now turning to the figures, FIGS. 5, 5A, 6 and 13 illustrate an embodiment of a bone cutter 20 of the present invention. As shown, the bone cutter comprises a bone cutter proximal end 22 that extends to a bone cutter distal end 24 along a longitudinal axis A-A. As illustrated, the bone cutter 20 of the present invention comprises a housing 26 that is designed to hold and secure a plurality of cutting blades that are used to cut and reshape the end of a bone 10, more specifically a femur (FIG. 4).

In an embodiment, the housing 26 comprises a first housing segment 28 that is connected to a second housing segment 30. The first housing segment 28 comprises a first blade holder proximal end 32 that extends along longitudinal axis A-A to a first housing segment distal end 34. The second housing segment 30 comprises a second housing segment proximal end 36 that extends along longitudinal axis A-A to a second housing segment distal end 38. A shaft portion 40 having spaced apart proximal and distal shaft ends 42, 44 extends in a proximal direction along longitudinal axis A-A from the second blade holder segment proximal end 36. As shown in FIG. 6, the first housing segment 28 is positioned distal of the second housing segment 30, the distal end 38 of the second housing segment positioned in contact with the proximal end 32 of the first housing segment 28.

In a preferred embodiment, a first blade or post cutting blade 46 and a second or chamfer blade 48 are held and secured by the first housing segment 28. A third or plan blade 50 is held and secured by the second housing segment 30. Thus, by connecting the first and second blade housing segments 28, 30 together, all three blades 46, 48, and 50 work in concert to form the head of a femur 10 into the desired shape as illustrated in FIG. 4.

Figure 7:
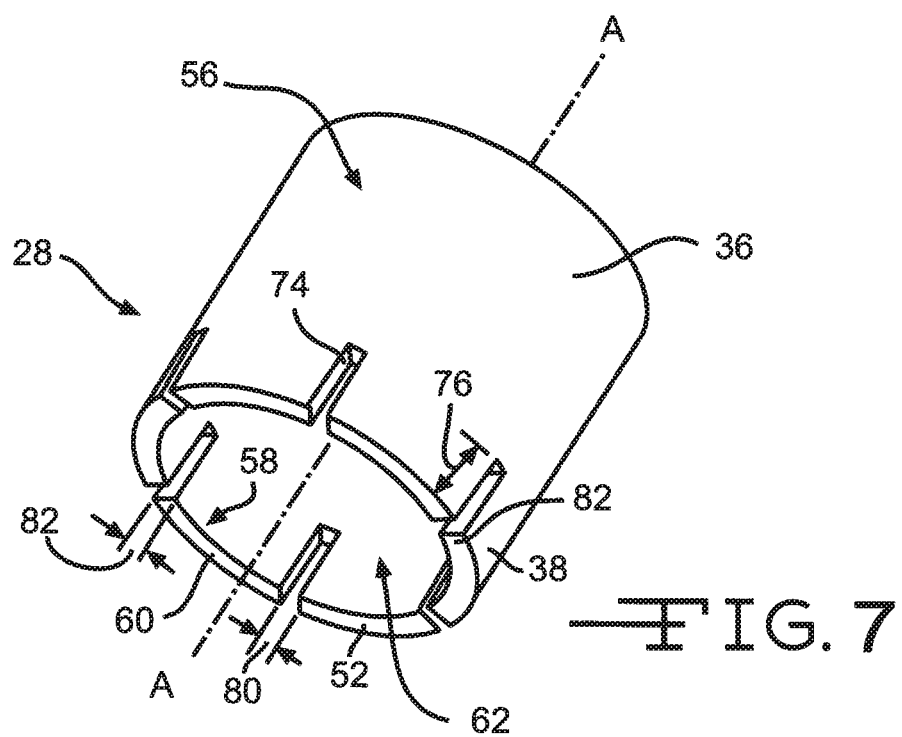
FIGS. 7 and 7A illustrate perspective views of an embodiment of the first housing segment of the bone cutter.

FIGS. 7, 7A, 7B, 8 and 8A illustrate an embodiment of the first housing segment 28 of the present invention. As shown, the first housing segment 28 is preferably of a cylindrical form having a first housing segment annular sidewall 52 that extends distally along longitudinal axis A-A from a first housing segment base 54. In a preferred embodiment, the sidewall 52 has an exterior sidewall surface 56 that extends to an interior sidewall surface 58. A sidewall thickness 60 resides therebetween. The annular sidewall 52 of the first housing segment 28 defines a cavity 62 which is intended to be positioned over the femur end. As shown in FIGS. 7 and 8A, the sidewall thickness 60 extends about perpendicular to longitudinal axis A-A. The interior sidewall surface 58 of the first housing segment 28 defines an inner diameter 64. In a preferred embodiment, the inner diameter 64 ranges from about 1 cm to about 15 cm. Since the inner diameter 64 defines the spacing and arrangement of the first cutting blades 46 which provide the cylindrical shape to the femur 10, the inner diameter 64 of the first housing segment 28 should be dimensioned accordingly.

As illustrated in FIGS. 5A, 7A, 7B, 8, and 8A, an opening 66 extends lengthwise along longitudinal axis A-A through a thickness 68 of the base 54 of the first housing segment 28. The opening 66 preferably provides a space for at least a portion of the second blade holder 30 to extend therethrough. In addition, the opening 66 provides a space for a guide rod 70 (FIG. 13) to extend therethrough.

In a preferred embodiment, the opening 66 provides a keyed interface within which the second housing segment 30 is received. As shown in FIG. 7B, which illustrates an end view of the first housing segment 28, the opening 66 is preferably constructed having a cross-section, oriented perpendicular with respect to longitudinal axis A-A, that enables the second housing segment 30 to mate and engage therewithin. Once joined, rotation of the second housing segment 30 imparts a rotational torque to the first housing segment 28.

In a preferred embodiment, as illustrated in FIG. 7B, the opening 66 of the base 54 of the first housing segment 28 comprises a cross-section, oriented perpendicular to longitudinal axis A-A, that is of a multi-sided polygon geometric shape, such as a triangle, a rectangular, a star, or octagon. This preferred embodiment enables the distal end 38 of the second housing segment 30, having a corresponding geometric shape, to mate and reside therewithin. In a preferred embodiment, an exterior sidewall or plurality of sidewalls of the second housing segment 30 is in physical contact with an interior surface 72 of the first housing segment opening 66 forming an interference fit therebetween. This interference relationship is preferred so that torque transfer between the blade holder segments 28, 30 is maximized.

As illustrated in FIGS. 5, 5A, 6, 7, 7A, 8 and 8A, at least one sidewall slot 74 extends through a portion of the thickness 60 of the sidewall 52 of the first housing segment 28. In a preferred embodiment, a plurality of sidewall slots 74, spaced apart from each other, reside about the perimeter of the distal end 34 of the first housing segment 28. The sidewall slot 74 is designed and dimensioned to receive and secure the first cutting blade 46 therewithin. Preferably, one sidewall slot 74 receives one first cutting blade 46. As shown, the sidewall slot 74 extends through the distal end 34 of the first blade holder 28. The sidewall slot 74 comprises a slot length 76 that extends about parallel to longitudinal axis A-A. In a preferred embodiment, the sidewall slot length 76 extends at least partially through a height 78 of the annular sidewall 52 to a point proximal of the distal end 34 of the first blade holder 28. The sidewall slot 74 of the first housing segment 28 also comprises a slot width 80 that extends about perpendicular to longitudinal axis A-A. In a preferred embodiment, the slot length 76 and slot width 80 are dimensioned to securely hold the proximal end of the first blade 46 therewithin. In addition, the sidewall slot 74 of the fist housing segment 28 comprises a slot depth 82 that preferably extends through the entire thickness 60 of the sidewall 52. In a preferred embodiment, the length 76 of the sidewall slot 74 may extend from about 0.5 cm to about 5 cm. The width 80 of the sidewall slot 74 may extend from about 1 cm to about 10 cm.

Figure 7A:
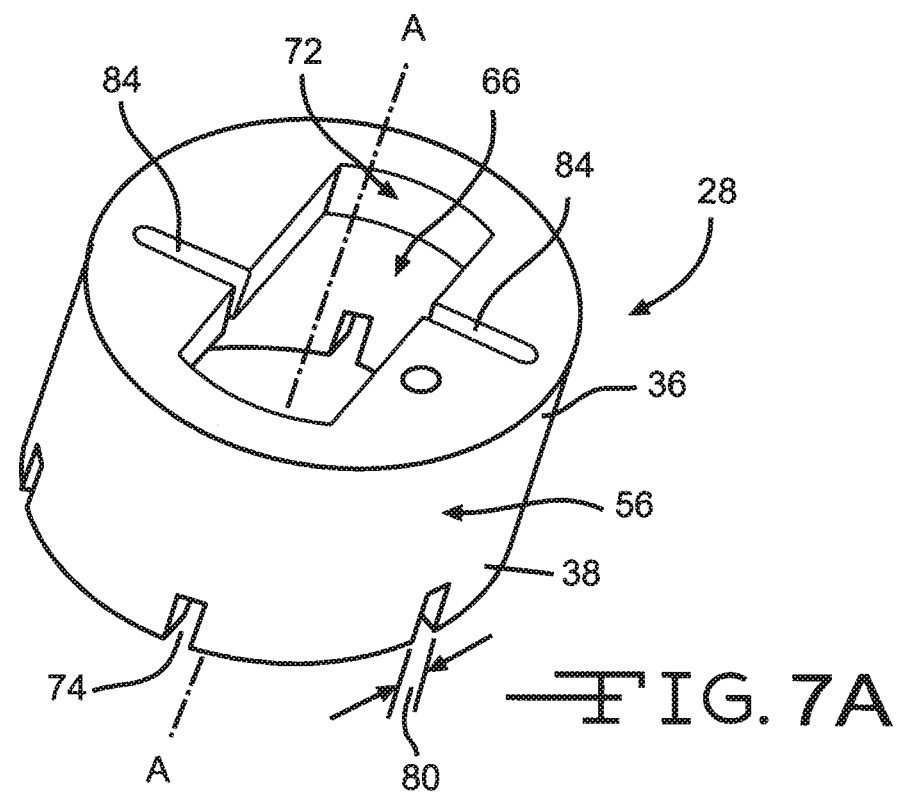
Figure 7B:
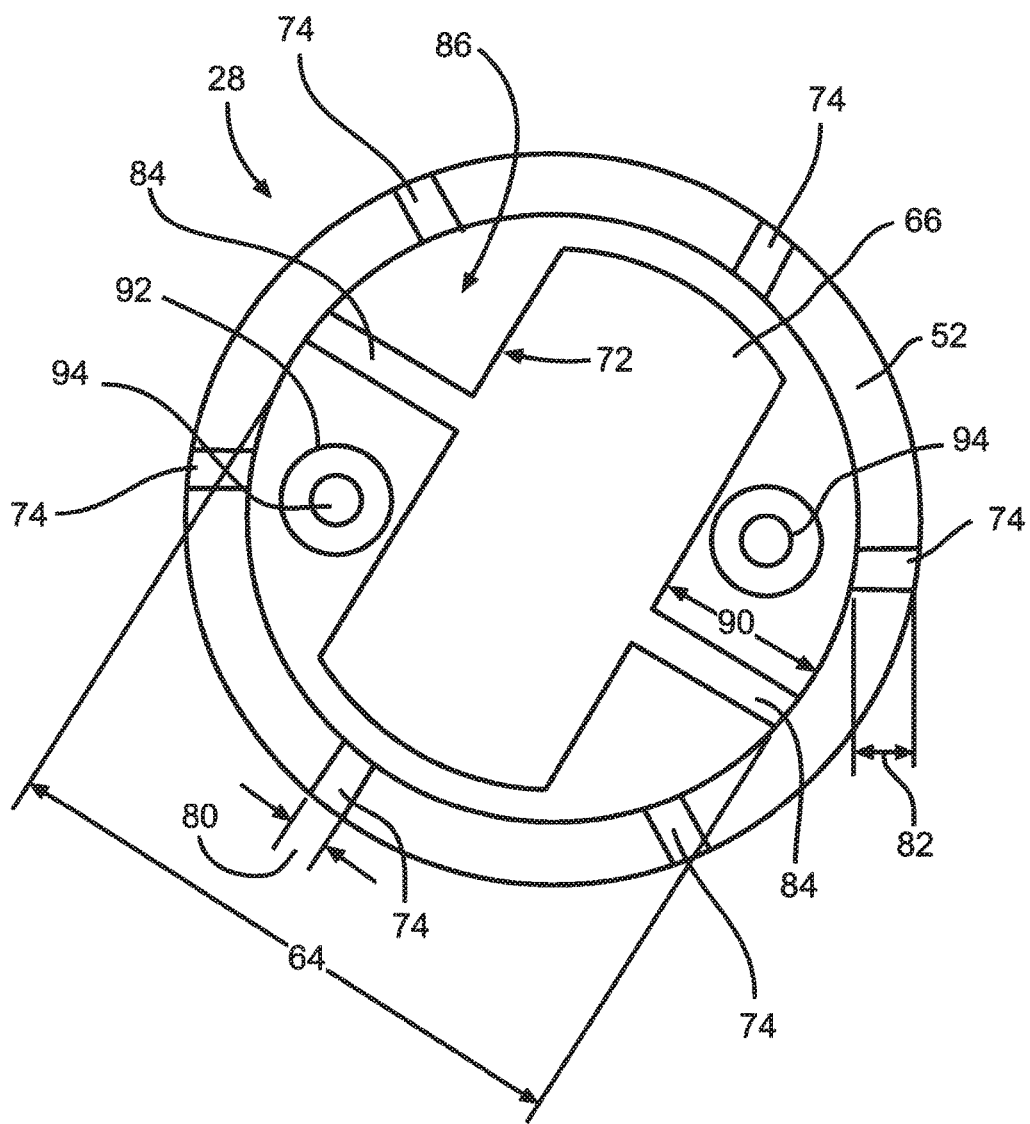
FIG. 7B shows an end view taken from the distal end of the first housing segment illustrated in FIGS. 7 and 7A.

As shown in FIGS. 7A and 7B, in addition to the sidewall slot 74, the first blade holder segment 28 comprises a base slot 84. In an embodiment, the base slot 84 extends through a top surface 86 of the base 54 of the first blade holder 28 and at least partially through the base thickness therewithin. In a preferred embodiment, the second blade 48 is received by the base slot 84 which holds and secures the blade therewithin. At least one base slot 84 is formed within the base 54 of the first housing segment 28. In a preferred embodiment, the base slot 84 comprises a base slot length 88 that extends at least partially through the thickness 66 of the base 54 parallel to longitudinal axis A-A. Alternatively, the length 88 of the base slot 84 may extend through the entire thickness 68 of the base 54 of the first housing segment 28. In addition, the base slot 84 comprises a base slot width 90 that extends about perpendicular to longitudinal axis A-A. In a preferred embodiment, the length 88 and/or the width 90 of the base slot 84 ranges from about 0.5 cm to about 5 cm.

In an embodiment, the first housing segment 28 may also comprise at least a throughbore 92 that extends through the thickness of the base along longitudinal axis A-A. The throughbore 92 provides an opening through which a fastener 94, such as a screw, a bolt or a rivet can be positioned therewithin to thereby join the first and second blade holder segments 28, 30 together. In an alternative embodiment, the first and second housing segments 28, 30 may be joined together using an adhesive or they may be welded together.

Figure 9A:
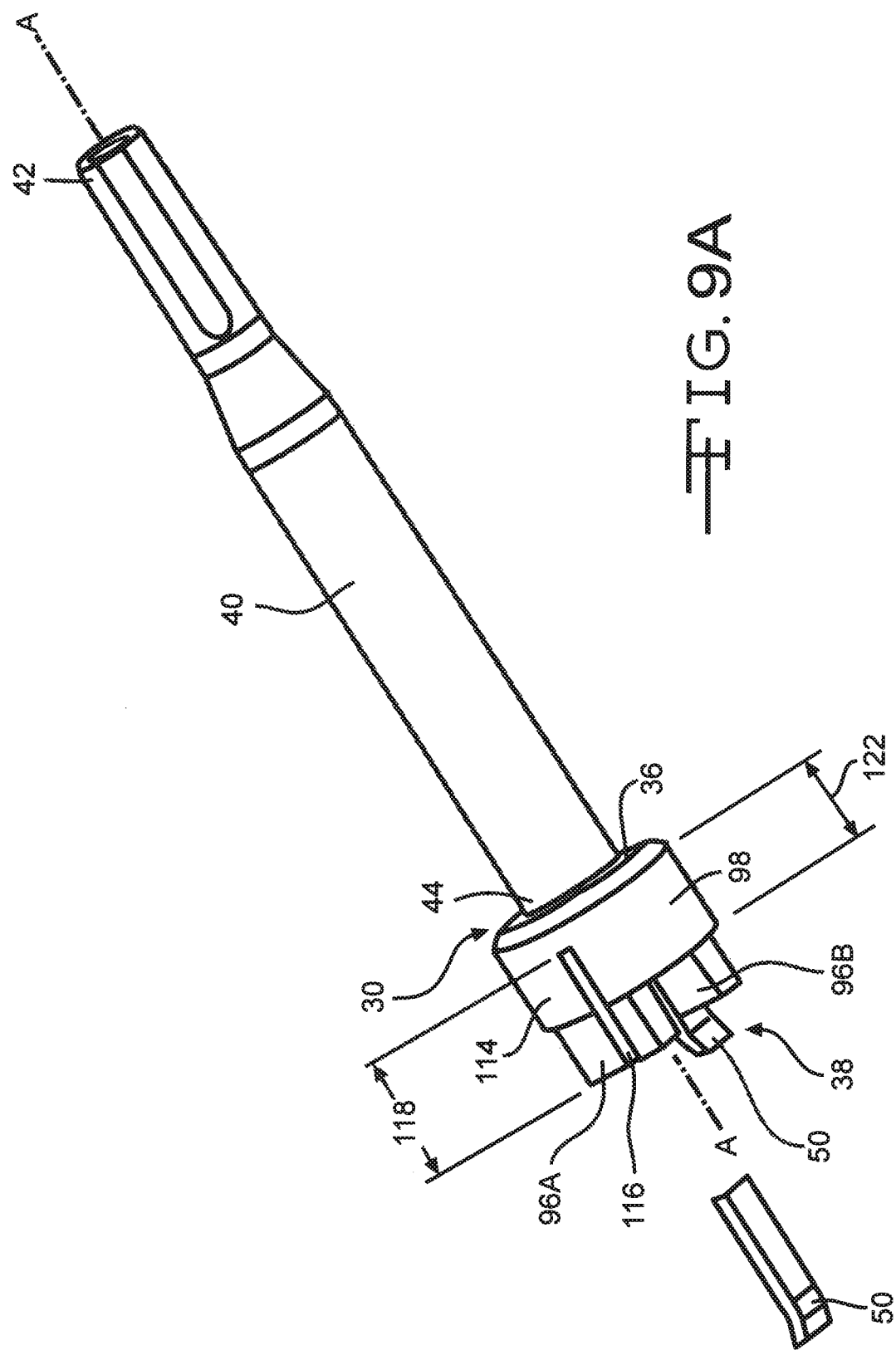
Figure 9B:
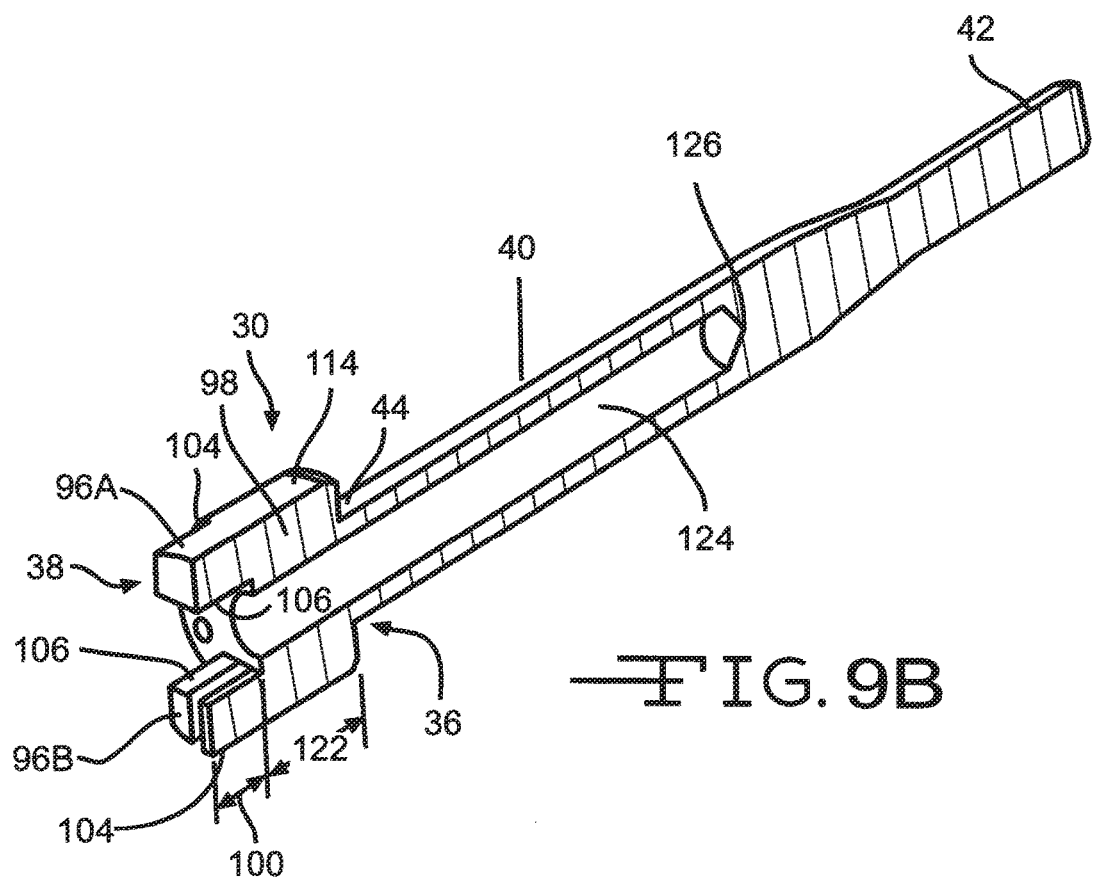
FIG. 9B is a cross-sectional view of the second housing segment shown in FIG. 9.
Figure 9C:
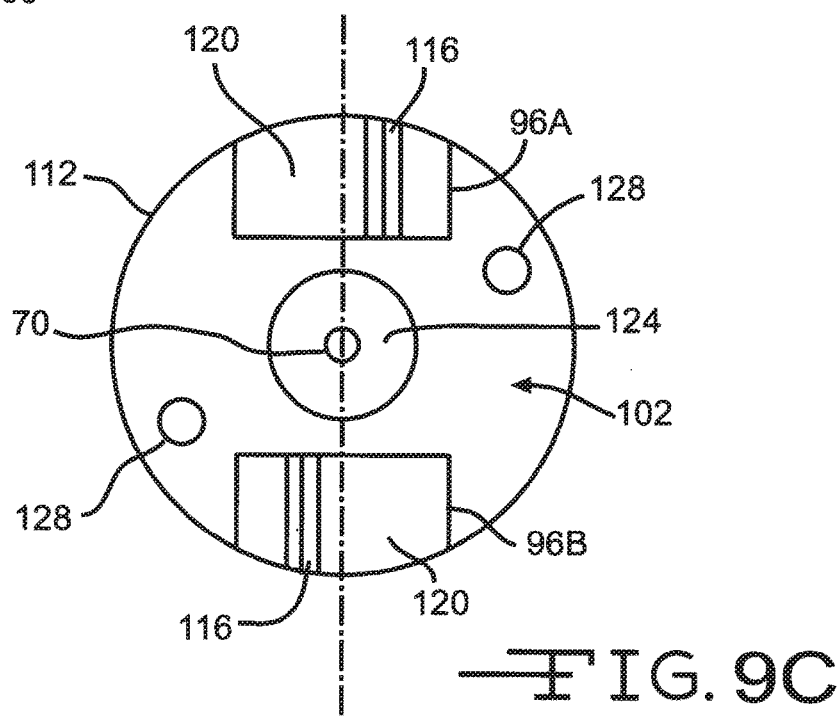
FIG. 9C shows an end view taken from the distal end of the second housing segment shown in FIG. 9.

FIGS. 9-9C illustrate an embodiment of the second housing segment 30 of the present invention. As shown in the embodiment the shaft portion 40 and the second blade holder 30 are constructed of a one piece body. However, in an alternative embodiment, the shaft 40 and the second housing segment 30 may be constructed as two separate bodies that are connected together. In this case, the distal end 44 of the shaft 40 would be connected to the proximal end 36 of the second housing segment 30.

As shown in FIGS. 9-9C, the second housing segment 30 comprises a blade holding platform 96 that extends distally along longitudinal axis A-A from a second base 98 of the second blade holder 30. Specifically, the blade holding platform 96 comprises a platform thickness 100 that extends distally from an end surface 102 (FIG. 9B). The thickness 100 of the platform 96 of the second base 98 extends parallel to longitudinal axis A-A. As shown in FIGS. 9 and 9B, the distal end 38 of the second housing segment 30, which engages the first housing segment 28, preferably comprises at least two platforms 96A, 96B that are spaced apart diametrically opposite from each other.

In a preferred embodiment, each of the platforms 96A, 96B comprises opposed first and second platform sidewalls 104, 106 that extend and meet opposed third and fourth platform sidewalls 108, 110. The first and second platform sidewalls 104, 106 are oriented perpendicular to the third and fourth platform sidewalls 108, 110. In a preferred embodiment, each of the platforms 96A, 96B are positioned so that the platform thickness 100 extends outwardly from the end surface 102 of the second base 98. In addition, each of the platforms 96A, 96B is designed to reside within a second base perimeter 112 (FIG. 9C) defined by the cross-sectional area of the distal end 38 of the second base 98. Furthermore, these platforms 96A, 96B are designed to at least partially extend through the opening 66 of the first base 54 of the first housing segment 28 to secure the second housing segment 30 therewithin. Therefore, it is preferred that the platforms 96A, 96B are positioned spaced from each other such that they fit through the aperture of the first base opening 66 of the first housing segment 28. In a preferred embodiment, shown in FIG. 9, the opposed third 108 and fourth 110 sidewalls of the platform 96 comprise planar surfaces. In a preferred embodiment, the planar surface of the third and fourth platform sidewalls 108, 110 are designed to contact the interior sidewall surface 72 of the opening 66 so that torque transferred between the second blade holder segment 30 and the first blade holder segment 28 occurs in unison.

In a preferred embodiment, each of the platforms 96A, 96B and the second base 98 may share a sidewall. As shown in the example of FIGS. 9 and 9B, platform 96A is positioned such that the first sidewall 104 and an exterior sidewall 114 of the second base 98 form one continuous sidewall.

As shown in FIGS. 9, 9A, and 9B a platform slot 116 at least partially extends through the thickness 100 of at least one of the platforms 96A, 96B. In an embodiment, the platform slot 116 may comprise a slot length 118 that extends longitudinally through an end surface 120 of the platform 96A, 96B and through at least a portion of the thickness 100 of the platform 96A, 96B to a position proximal of the distal end of the platform 96A, 96B.

The platform slot 116 is dimensioned so that the third cutter blade 50 is received and securely positioned therewithin. The platform slot 116 comprises a platform slot width 121 that extends at least partially through a width of the platform 96A, 96B (FIG. 9). In a preferred embodiment, the length 118 of the platform slot 116 may extend through the thickness 100 of the platform 96A, 96B and through a portion of a thickness 122 of the base 98 of the second blade holder 30. The slot 116 is oriented such that the platform slot length 118 is positioned parallel to longitudinal axis A-A and the platform slot width 121 is positioned perpendicular to the longitudinal axis A-A.

As illustrated in FIGS. 9, 9B and 9C, an inlet 124 extends through the distal end surface 102 of the second base 98 of the second blade holder 30 in a proximal direction parallel to longitudinal axis A-A. The inlet 124, which preferably lies co-axial the longitudinal axis A-A, provides a space in which the guide rod 70 may extend. In a preferred embodiment, the inlet 124 extends through the thickness 122 of the base 98 and through at least a portion of the thickness within the shaft 40. In a preferred embodiment, a proximal end 126 of the inlet 124 resides within the shaft 40 between the proximal and distal shaft ends 42, 44.

In a preferred embodiment, both the first and second blade housing segments 28, 30 are composed of a biocompatible material. In a preferred embodiment, the housing segments 28, may be composed of a polymeric material such as acroylonitirile butadiene styrene (ABS), polyarylamide, polyetheretherketone (PEEK), and combinations thereof. Alternatively, the first and second blade holder segments 28, 30 may be comprised of a metallic material, examples of which include, but are not limited, to stainless steel, MP35N, titanium, and combinations thereof.

In addition, as shown in FIG. 9C, the second blade holder segment 30 may comprise at least one second blade holder throughbore 128 which extends longitudinally through the second base 98 of the second holder 30. In a preferred embodiment, the second blade holder throughbore 128 is designed to provide an opening for the fastener 94 that connects the second blade holder 30 to the first holder 28.

Figure 5:
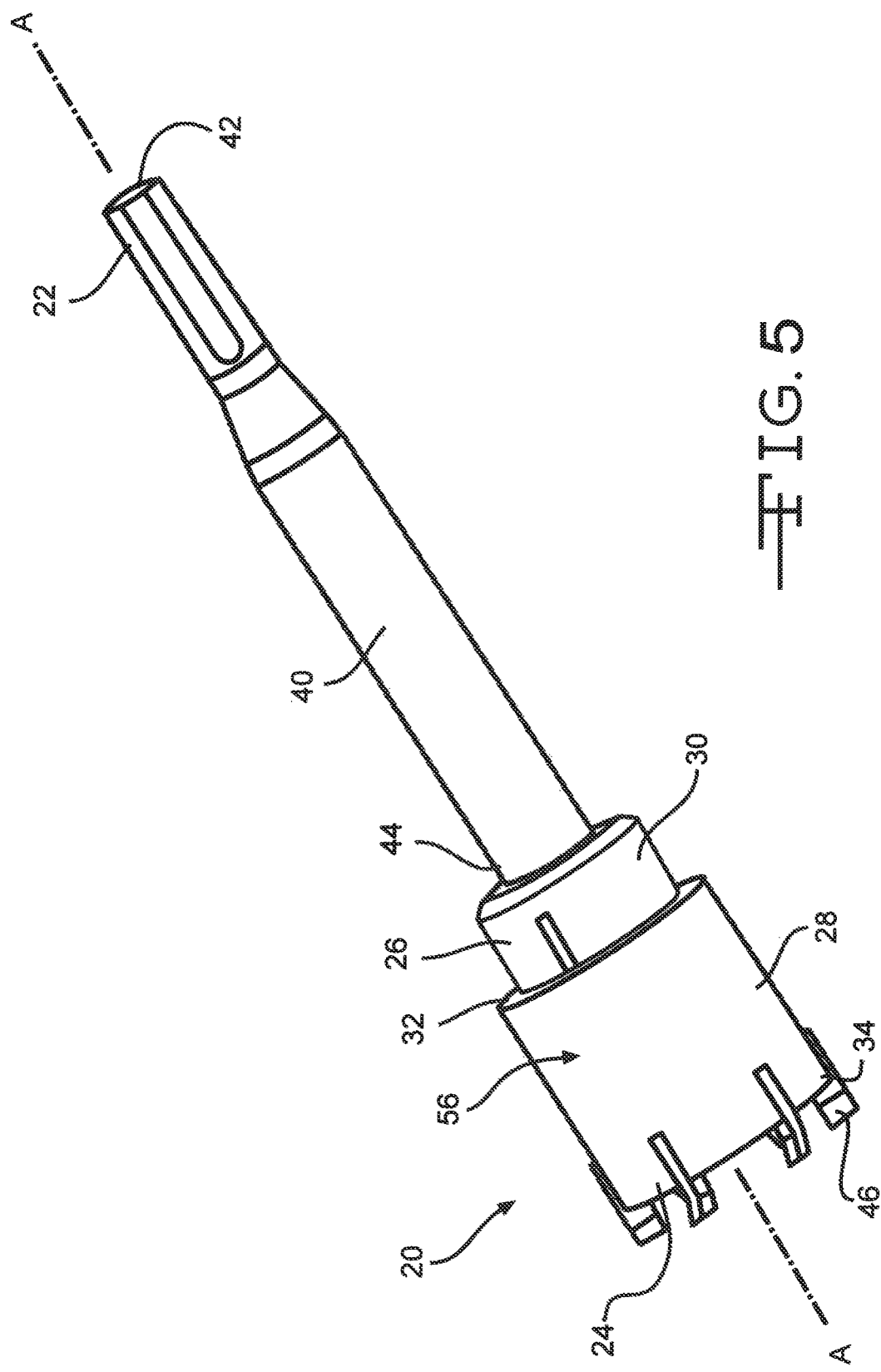
FIG. 5 shows a perspective view of an embodiment of the bone cutter of the present invention.
Figure 5A:
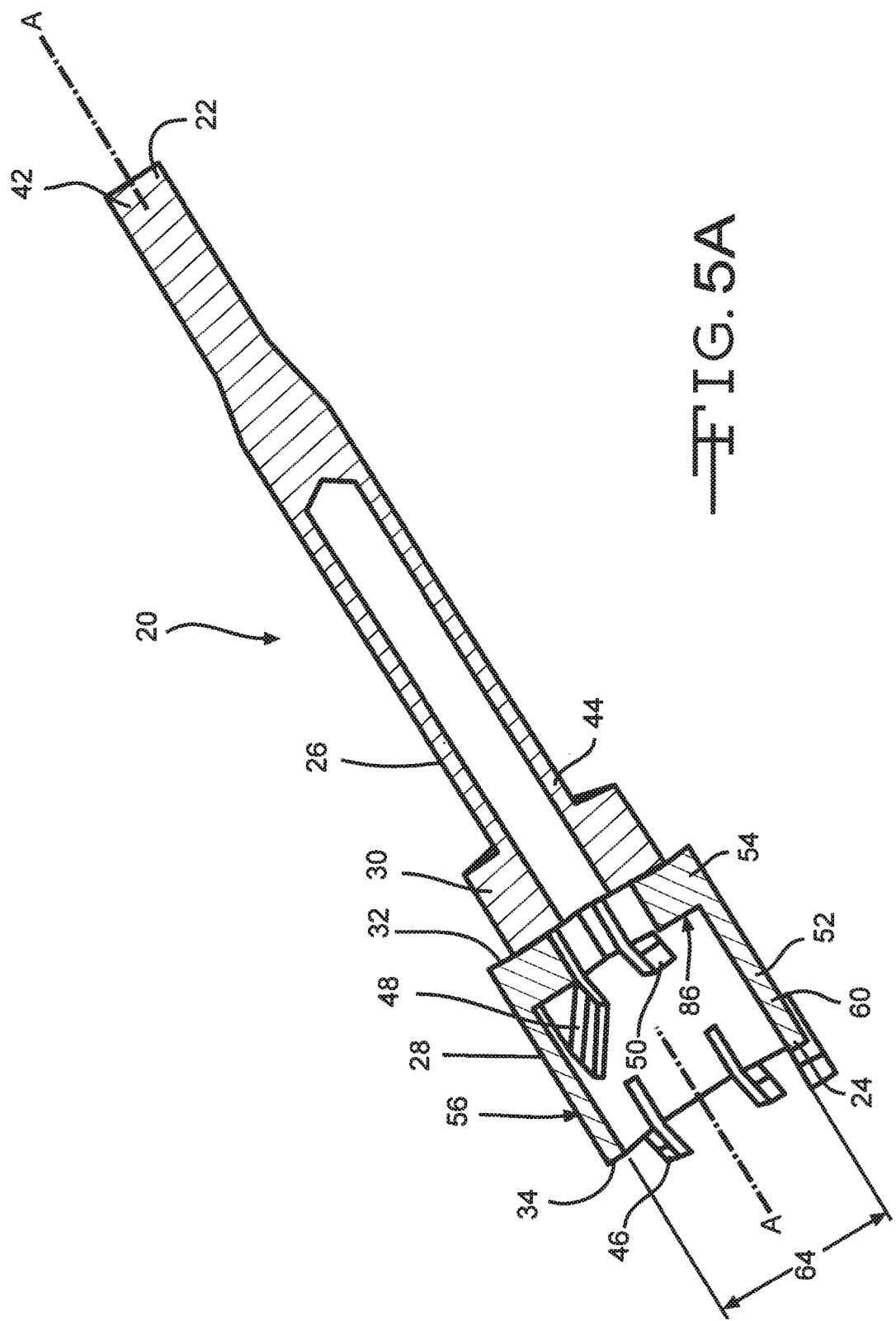
FIG. 5A illustrates a cross-sectional view of the bone cutter shown in FIG. 1.
Figure 10:
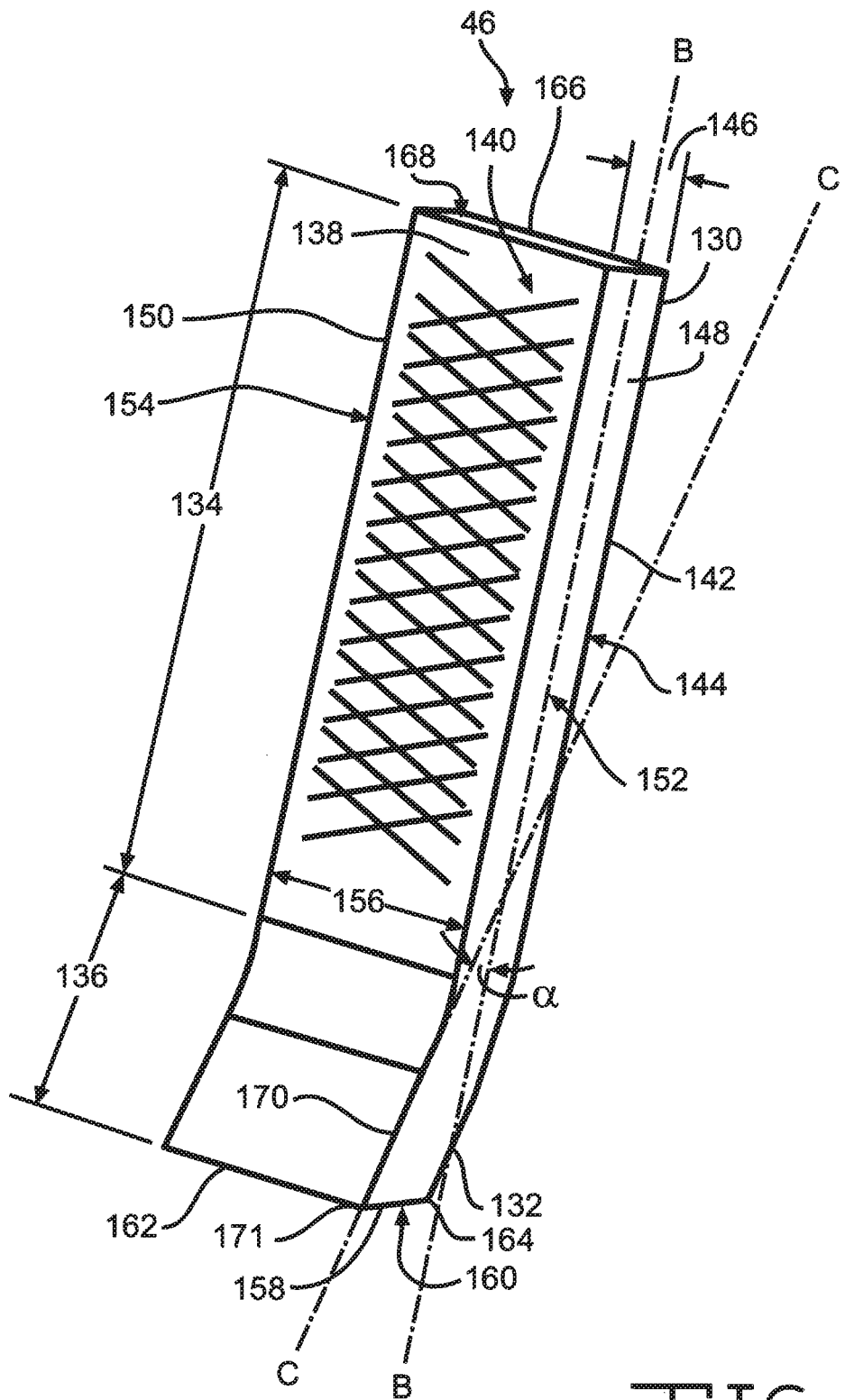
FIG. 10 illustrates a perspective view of an embodiment of the first cutting blade.

FIG. 10 illustrates an enlarged view of an embodiment of the first blade 46. As shown, the first blade 46 comprises a first blade proximal end 130 spaced from a first blade distal end 132. More specifically, the first blade 46 comprises a first blade holder engagement portion 134 located at the proximal end 130 of the blade 46 and that extends to a first blade cutting portion 136 that resides at the distal end 132 of the first blade 46. As illustrated in FIGS. 5, 5A and 6, the first blade engagement portion 134 is preferably positioned within the sidewall slot 74 of the first blade holder 28.

In a preferred embodiment, the first blade 46 comprises a first sidewall 138 having a first exterior surface 140 that is spaced from a second sidewall 142 having a second exterior surface 144. A first blade thickness 146 extends therebetween. As illustrated in FIG. 10, an imaginary line B-B extends parallel to the opposed first and second sidewalls 138, 142 through the thickness 146 of the blade engagement portion 134. In a preferred embodiment, imaginary line B-B extends substantially through the middle of the thickness 146 between the opposed first and second sidewalls 138, 142, thereby bisecting the thickness 146 of the first blade 46 within the first blade holder engagement portion 134. In addition, the first blade 46 comprises opposed third and fourth sidewalls 148, 150 having respective third and fourth exterior surfaces 152, 154 that are oriented perpendicular to the opposed first and second sidewalls 138, 142. A first blade width 156 extends between the third and fourth sidewalls 148, 150. Preferably, the first and second exterior surfaces 140, 144 may be planar having a knurled surface particularly within the blade holder engagement portion. This preferred construction of the blade engagement portion 134 helps ensure a secure fit within the sidewall slot 74 of the first housing segment 28.

The cutting portion 136 of the first blade 46 extends distally from the first blade engagement portion 134 to a first blade distal end sidewall 158 having a distal end surface 160. The distal end of the first sidewall 138 extends and meets the distal end sidewall 158 at a first blade cutting edge 162. The distal end of the second sidewall 142 extends and meets the distal end sidewall 158 at a first blade trailing edge 164. In a preferred embodiment, the first blade cutting edge 162 is oriented perpendicular to the line B-B. In addition, the first blade distal end sidewall 158 is also oriented perpendicular to the line B-B. At the proximal end 130 of the first blade 46, the proximal end of the first and second sidewalls 138, 142 extend and meet at a first blade proximal end sidewall 166 having a first blade proximal end surface 168.

As illustrated in FIG. 10, the cutting portion 136 of the first cutting blade 46 is preferably bent at an angle away from the line B-B. More specifically, the cutting portion 136 of the first cutting blade 46 is bent at a rake angle α. The rake angle α of the cutting portion 136 of the first blade 46 is defined by the angle that extends between imaginary line C-C and line B-B. As shown in FIG. 10, imaginary line C-C is coincident a first side edge 170 that is formed at the meeting of the first sidewall 138 and the third sidewall 148 within the cutting portion 136. As shown, imaginary line C-C extends through a first intersection point 171 where the first cutting edge 162 and the third sidewall 170 meet. In a preferred embodiment, the rake angle α ranges from about 50 to about 40°. The perpendicular orientation of the first cutting edge 162 with respect to line B-B in addition to the rake angle α that efficiently removes bone material from the end of the femur so that the post 268 and platform surface 270 illustrated in FIG. 4 are formed.

As shown in FIGS. 5, 5A and 6, each of the first blades 46 are positioned within their respective sidewall slot 74 of the first housing segment 28. In a preferred embodiment, the blade holder engagement portion 134 is positioned within the slot 74 so that the line B-B is positioned about parallel with longitudinal axis A-A. In addition, when positioned within the slot 74, the cutting edge 162 of the first blade 46 is positioned about perpendicular to longitudinal axis A-A.

Figure 11:
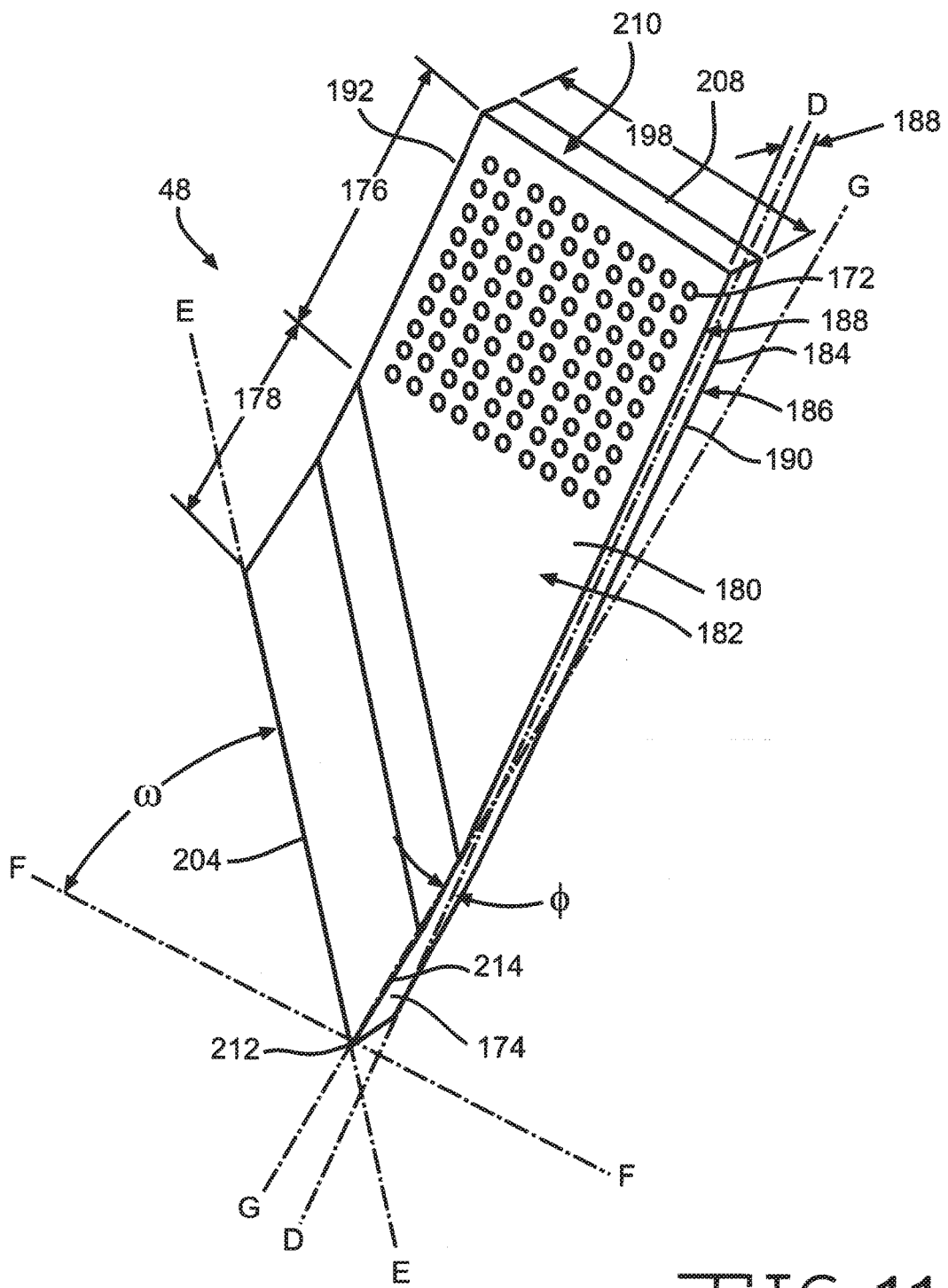
FIG. 11 is a perspective view of an embodiment of the second cutting blade.

FIG. 11 illustrates a magnified view of an embodiment of the second blade 48. The second blade 48, also referred to as a chamfer blade, is designed to impart a chamfered edge 272 to the proximal end of the cylindrically reshaped femur as illustrated in FIG. 4. As shown, the second blade comprises a proximal end 172 that extends to a distal end 174. More specifically, the second blade 48 comprises a second blade holder engagement portion 176 that extends to a second blade cutting portion 178. As illustrated in FIG. 5A, the second blade engagement portion 176 is preferably positioned within the first base slot 84 of the first blade holder 98.

In a preferred embodiment, the second blade 48 comprises a first sidewall 180 having a first exterior surface 182 that is spaced from a second sidewall 184 having a second exterior surface 186. A second blade thickness 188 extends therebetween. As illustrated in FIGS. 11, 11B and 11C, an imaginary line D-D extends parallel to the first and second sidewalls 180, 184 through the thickness 188 of the blade engagement portion 176, and about mid-way through the thickness 188 of the second blade 48 within the second blade holder engagement portion 176. In addition, the second blade 48 comprises opposed third and fourth sidewalls 190, 192 having respective third and fourth exterior surfaces 194, 196 that are oriented perpendicular to the opposed first and second sidewalls 180, 184. A second blade width 198 extends between the third and fourth sidewalls 190, 192. Preferably, the first and second exterior surfaces 182, 186 may be planar having a knurled surface particularly within the blade holder engagement portion. This preferred construction of the blade engagement portion 176 helps ensure a secure fit within the base slot 84 of the first blade holder 28.

The cutting portion 178 of the second blade 48 extends distally from the second blade holder engagement portion 176 to a second blade distal end sidewall 200 having a distal end surface 202. The distal end of the first sidewall 180 extends and meets the distal end sidewall 200 at a second blade cutting edge 204. The distal end of the second sidewall 184 extends and meets the distal end sidewall 200 at a second blade trailing edge 206. At the proximal end 172 of the second cutting blade 48, the proximal end of the first and second sidewalls 180, 184 extend and meet at a second blade proximal end sidewall 208 having a second blade proximal end surface 210.

Figure 11A:
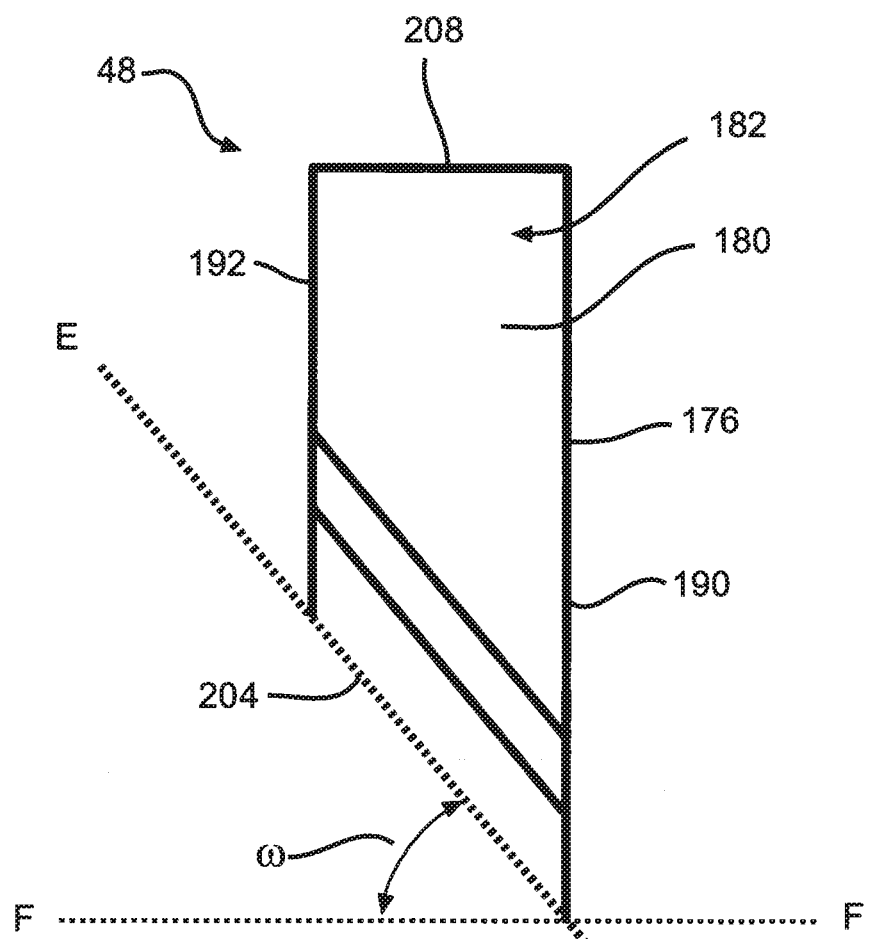
FIG. 11A is a side view taken from the first sidewall of the second cutting blade shown in FIG. 11.
Figure 11B:
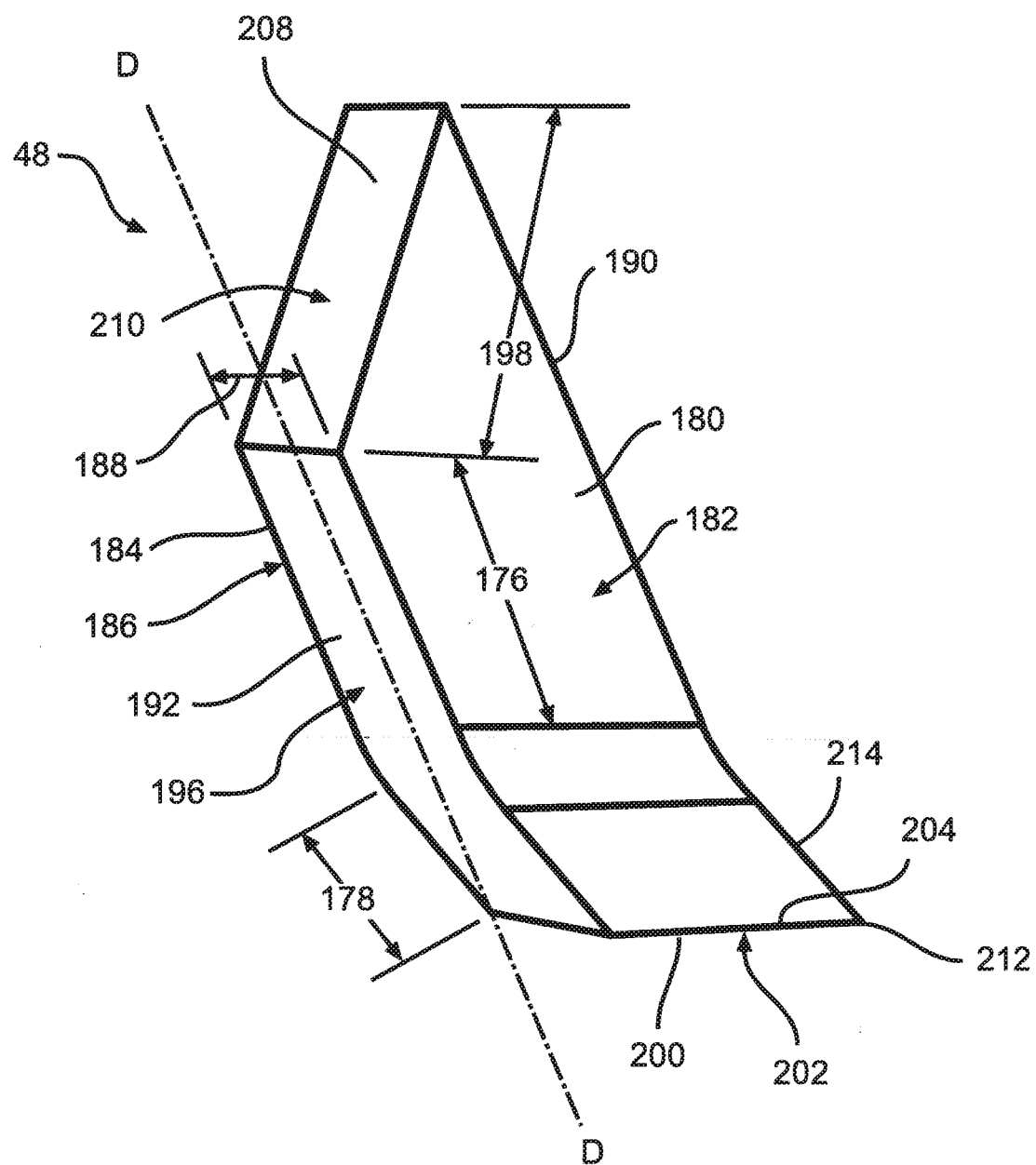
FIGS. 11B and 11C are additional perspective views of the second cutting blade shown in FIG. 11.
Figure 11C:
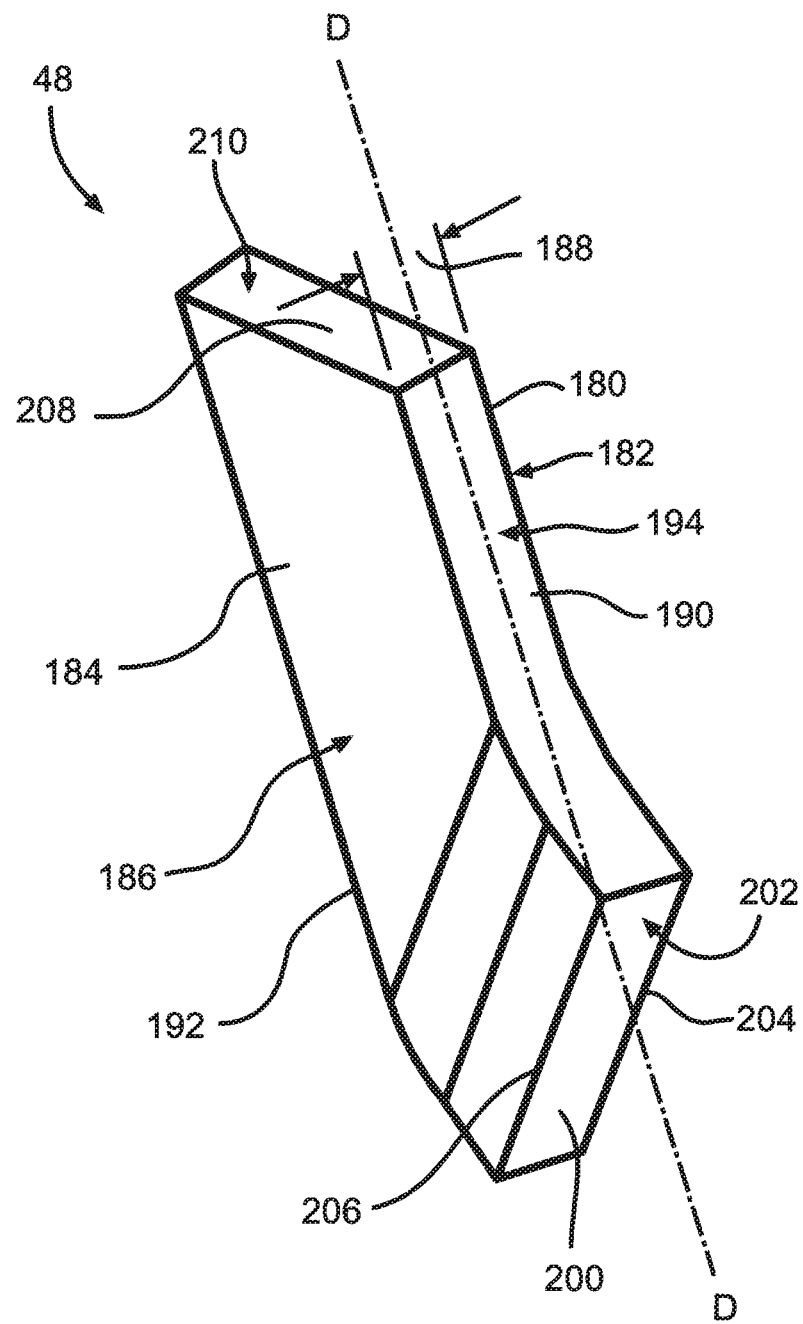

As shown in FIGS. 11 and 11A, a first imaginary line E-E lies coincident along the second blade cutting edge 204 extending widthwise across the blade 48. In addition, a second imaginary line F-F oriented perpendicular to the line D-D, extends through a second intersection point 212 that resides at the intersection of the distal end of a second blade first edge 214 and the second blade cutting edge 204. The first edge 214 defined by the intersection of the first sidewall 180 and the third sidewall 190 of the second blade 48. Furthermore, a third imaginary line G-G is shown that is coincident the first edge 214 of the second cutting blade 48 that extends through the second intersection point 212 that resides at the distal end of the second blade 48.

As illustrated in FIGS. 11, 11B, and 11C, in a preferred embodiment, the cutting portion 178 of the second cutting blade 48 is preferably bent at an angle away from the line D-D. More specifically, the cutting portion 178 of the second cutting blade 48 is bent at a second rake angle ϕ. The second rake angle ϕ is defined by the angle that extends between the third imaginary line G-G and line D-D. In a preferred embodiment, the second rake angle ϕ ranges from about 50 to about 40°.

In addition, the second cutting blade 48 further comprises a chamfer angle ω. In a preferred embodiment, illustrated in. FIG. 11, the chamfer angle ω is defined as the angle that extends between imaginary line E-E and imaginary line F-F. In a preferred embodiment, the chamfer angle ω ranges from about 5° to about 40°. The chamfer angle ω is designed to impart a chamfer at the distal end of the femur 10. The second cutting blade 48 is designed so that the chamfer angle ω of the second blade 48 creates a chamfered surface 272 (FIG. 4) at the end of the reshaped cylindrical end of the femur that is angled at the same angular degree as the chamfer angle ω of the second cutting blade 48.

As shown in FIG. 8A, each of the second blades 48 are positioned within their respective base slot 84 of the first blade holder 28. In a preferred embodiment, the blade holder engagement portion 176 of the second cutting blade 48 is positioned within the slot 84 so that the line D-D is positioned about parallel with longitudinal axis A-A.

Figure 12:
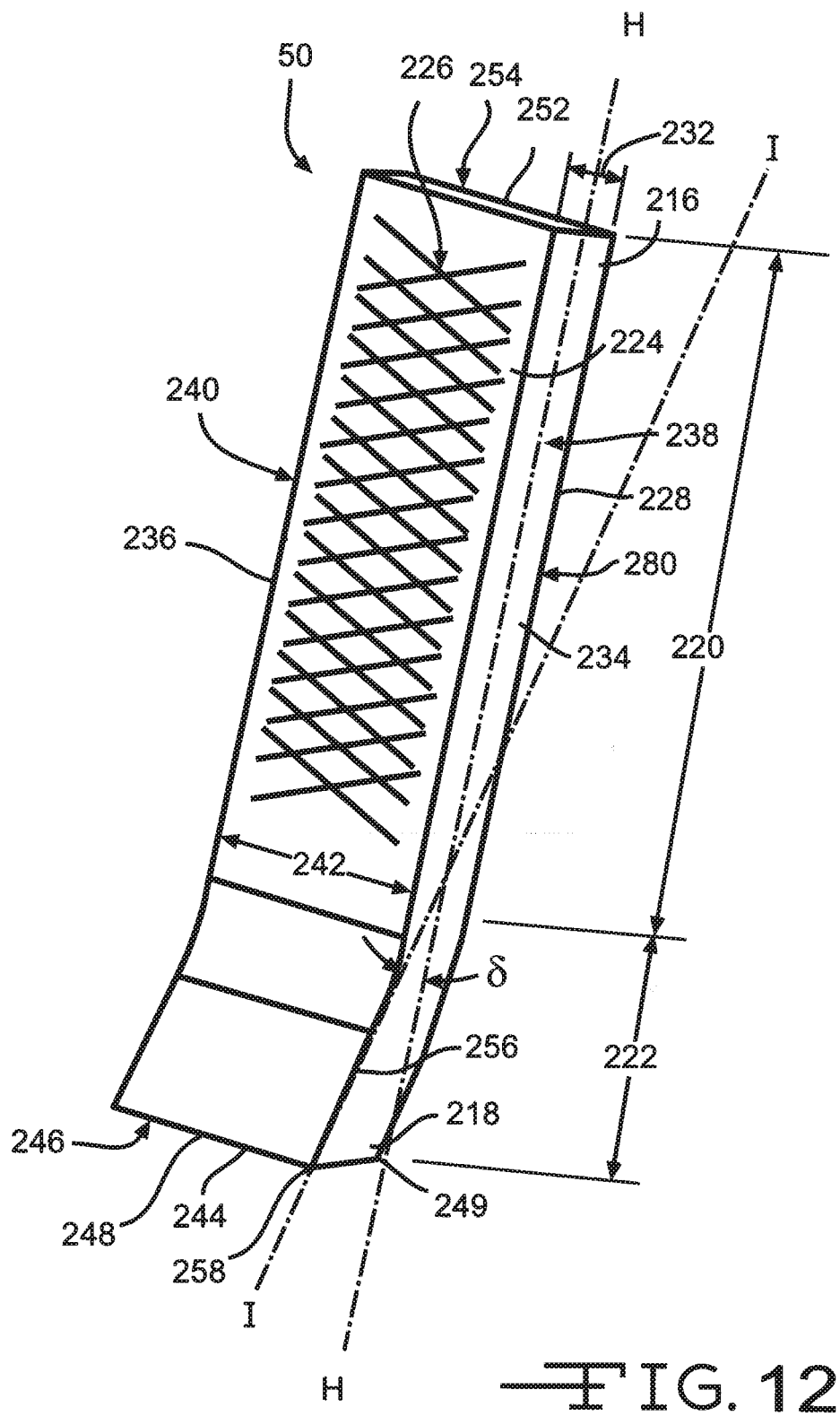
FIG. 12 illustrates a perspective view of an embodiment of the third cutting blade.

FIG. 12 illustrates an enlarged view of an embodiment of the third blade 50. As shown, the third blade 50 comprises a third blade proximal end 216 spaced from a third blade distal end 218. More specifically, the third blade 50 comprises a third blade holder engagement portion 220 located at the proximal end 216 of the blade 50 that extends to a third blade cutting portion 222 that resides at the third blade distal end 218. As illustrated in FIG. 9A, the third blade engagement portion 220 is preferably positioned within the platform slot 116 of the second blade holder 30.

In a preferred embodiment, the third blade 50 comprises a first sidewall 224 having a first exterior surface 226 that is spaced from a second sidewall 228 having a second exterior surface 230. A third blade thickness 232 extends therebetween. As illustrated in FIG. 12, an imaginary line H-H extends parallel to the first and second sidewalls 224, 228 through the thickness 232 of the blade engagement portion 220, thereby bisecting the thickness 232 of the holder engagement portion 220 of the third blade 50. In addition, the third blade 50 comprises opposed third and fourth sidewalls 234, 236 having respective third and fourth exterior surfaces 238, 240 that are oriented perpendicular to the opposed first and second sidewalls 224, 228. A width 242 extends between the third and fourth sidewalls 234, 236 of the third blade 50. Preferably, the first and second exterior surfaces 226, 230 may be planar having a knurled surface, particularly within the blade holder engagement portion 220. This preferred construction of the blade engagement portion 220 of the third blade 50 helps ensure a secure fit within the platform slot 116 of the second blade holder 30.

The cutting portion 222 of the third blade 50 extends distally from the third blade holder engagement portion 220 to a third blade distal end sidewall 244 having a distal end surface 246. The distal end of the first sidewall 224 of the third blade 50 extends and meets the third blade distal end sidewall 244 at a third blade cutting edge 248. The distal end of the second sidewall 228 extends and meets the distal end sidewall 244 at a third blade trailing edge 249. In a preferred embodiment, the third blade cutting edge 248 is oriented perpendicular to the line H-H. In addition, the third blade distal end sidewall 244 also resides perpendicular to the line H-H. In a preferred embodiment, the proximal end of the first and second sidewalls 224, 228 extend and meet at a third blade proximal end sidewall 252 having a third blade proximal end surface 254.

As illustrated in FIG. 12, the cutting portion 222 of the third cutting blade 50 is preferably bent at an angle away from the line H-H. More specifically, the cutting portion 222 of the third cutting blade 50 is bent at a third rake angle δ. The third rake angle δ of the third blade 50 is defined by the angle that extends between imaginary line I-I and line H-H. As shown in FIG. 12, imaginary line I-I is coincident a first side edge 256 of the third blade 50 that is formed at the meeting of the first sidewall 224 and the third sidewall 234 that extends through intersection point 258 where the third cutting edge 248 and the third sidewall 234 meet. In a preferred embodiment, the third rake angle δ ranges from about 50 to about 40°.

As shown in FIG. 9A, each of the third blades 50 are positioned within their respective platform slot 116 of the second blade holder 30. In a preferred embodiment, the blade holder engagement portion 220 of the third cutting blade 50 is positioned within the platform slot 116 so that the line H-H is positioned about parallel with longitudinal axis A-A. In addition, when positioned within the slot 116, the cutting edge 248 of the third blade 50 is preferably positioned about perpendicular to longitudinal axis A-A.

Referring back to FIG. 5A, when the cutting blades 46, 48, and 50 are properly positioned within the housing 26 of the cutting tool 20 of the present invention, the first cutting edge 162 of the first cutting blade 46 resides distal of the second and third cutting edges 204, 248 of the second and third blades 48, 50 respectively. As shown, the first cutting edge 162 extends beyond the distal end 34 of the first blade holder 28. In addition, the second cutting edge 204 of the second blade 48 resides distal of the third cutting edge 248 of the third blade 50 within the cavity 62 of the first blade holder segment 28.

As previously discussed, FIG. 4 illustrates a desired shape 250 of the reshaped femur 10 that is ready to receive a femoral head prosthesis. As shown, the end of the femur has been reshaped to comprise a post 260 having a proximal post end 262 that extends to a distal post end 264 that is designed to receive a femoral head prosthesis (not shown). Specifically, the femoral head prosthesis is designed to be positioned over and secured to the post 260. As illustrated, the post 260 comprises a cylindrical portion 266 having a cylindrical sidewall 268 that extends outwardly from a bone platform surface 270. The bone platform surface 270 preferably comprises a planar surface to ensure proper fit of the femoral head prosthesis (not shown). In addition, the post 260 comprises a chamfer portion 272 that resides at the distal end of the post 260.

As illustrated in FIG. 13, in a preferred embodiment, the first cutting edge 162 of the first cutting blade 46 of the present invention forms the cylindrically shaped post 260 and planar surfaced bone platform 270. The second cutting edge 204 of the second or chamfer blade 48 imparts the chamfered surface 272 located at the distal end 264 of the post 260. Lastly, the third cutting edge 248 of the third or plane cutting blade 50 imparts a planar surface 274 that resides at the distal end 264 of the post 260 of the reshaped femur 10.

Rotation of the first blade holder 28 along with the first and second blades 46, 48 shape the end of a femur 10 into the form of a post 260 in one cutting event or procedure. As the cutting tool 20 of the present invention is rotated against the end of the bone, all three blades 46, 48, 50 cut their respective portions of the femur at the same time. In other words, the first blade 46 forms the sidewall of the post end 260, the second blade 48 forms the chamfered surface 272 at the distal post end 264 and the third blade 50 forms the planar surface 274 at the distal end of the femur.

While the preferred embodiments of the cutting device and methods have been described in reference to the environment in which they were developed, they are merely illustrative of the principles of the inventions. Other embodiments and configurations may be devised without departing from the spirit of the inventions and the scope of the appended claims.

What is claimed is:

1. A bone cutter, comprising:
    a) a housing that extends along a longitudinal axis, the housing comprising:
        i) a first housing portion having an annular sidewall that extends from a first base, wherein a first slot extends through at least a portion of the first housing portion annular sidewall;
        ii) a second housing portion having a platform that extends from a second base, wherein a second slot extends at least partially through a thickness of the second housing portion platform; and
        iii) wherein the first and second housing portions are joined;
    b) a first cutting blade comprising:
        i) a first sidewall having a first blade engagement portion that extends to a first blade cutting portion, the first blade engagement portion received within the first housing portion slot, wherein a first blade thickness extends between opposed first and second sidewall surfaces, and opposed third and fourth sidewall surfaces oriented perpendicular to the first and second sidewall surfaces, and wherein a first cutting edge is formed where a distal end of the first sidewall surface and a distal end sidewall surface meet, the distal end sidewall surface residing between distal ends of the opposed first and second sidewall surfaces;
        ii) a first imaginary line oriented parallel to the longitudinal axis that extends substantially through a middle of the first blade thickness of the first blade engagement portion, wherein the first blade cutting portion is oriented at a rake angle with respect to the first blade engagement portion, the rake angle extending between the first imaginary line and a second imaginary line that is coincident with a first blade side edge formed at the intersection of the first sidewall surface and the third sidewall surface, the second imaginary line extending through a first blade intersection point where the cutting edge and the third sidewall surface meet; and
    c) a second cutting blade having a second blade engagement portion extending to a second blade cutting portion with a second blade cutting edge, wherein the second blade engagement portion is received within the second slot of the second housing portion; and
    d) wherein the bone cutter is configured to be rotated against a bone to cause the bone to be cut by the first and second cutting blades.

2. The bone cutter of claim 1 wherein the first blade cutting portion resides distal of the second blade cutting portion.

3. The bone cutter of claim 1 wherein the first cutting edge is oriented perpendicular to the longitudinal axis.

4. The bone cutter of claim 1 wherein the second cutting blade comprises a second sidewall having opposed fifth and sixth sidewall surfaces, a second cutting blade thickness therebetween, and opposed seventh and eighth sidewall surfaces oriented perpendicular to the opposed fifth and sixth sidewall surfaces, wherein the second cutting edge is formed where a distal end of the fifth sidewall surface and a distal end sidewall surface meet, the distal end sidewall surface residing between distal ends of the opposed first and second sidewall surfaces.

5. The bone cutter of claim 4 wherein the second cutting blade comprises a second rake angle that extends between a third imaginary line that resides substantially through a middle of the second cutting blade thickness of the second blade engagement portion and a fourth imaginary line that lies coincident with a second blade side edge, the second blade side edge formed at an intersection of the distal end of the fifth sidewall surface and the seventh sidewall surface.

6. The bone cutter of claim 1 wherein an opening extends along the longitudinal axis through a thickness of the first housing portion base, wherein the opening provides a space for at least a portion of the second housing portion to extend therethrough.

7. The bone cutter of claim 6 wherein the first housing portion base opening comprises a cross-section, oriented perpendicular to the longitudinal axis, that is of a multi-sided polygon geometric shape.

8. The bone cutter of claim 6 wherein at least a portion of the second housing portion platform is received and mates within the first housing portion base opening.

9. The bone cutter of claim 1 wherein the second slot of the second housing portion extends parallel to the longitudinal axis.

10. The bone cutter of claim 1 wherein a fastener joins the first and second housing portions together.

11. The bone cutter of claim 1 wherein a shaft portion having opposed proximal and distal shaft ends is joined to the second housing portion, the shaft distal end contacting a second housing portion proximal end.

12. The bone cutter of claim 11 wherein an inlet extends within a thickness of the shaft portion through the shaft distal end to a point distal of the shaft proximal end.

13. A bone cutter, comprising:
   a) a housing that extends along a longitudinal axis, the housing comprising:
      i) a first housing portion having an annular sidewall that extends from a first base;
      ii) a second housing portion having a platform that extends from a second base; and
      iii) wherein the first and second housing portions are joined;
   b) a first cutting blade comprising a first blade engagement portion extending to a first blade cutting portion having a first blade cutting edge, wherein the first blade engagement portion is received within a first slot that extends at least partially through the first housing portion annular sidewall;
   c) a second cutting blade comprising a second blade engagement portion extending to a second blade cutting portion having a second blade cutting edge, wherein the second blade engagement portion is received within a second slot that extends at least partially through a thickness of the first base;
   d) a third cutting blade comprising a third blade engagement portion extending to a third blade cutting portion having a third blade cutting edge, wherein the third blade engagement portion is received within a third slot that extends at least partially through the second housing portion platform; and
   e) wherein of the bone cutter is configured to be rotated against a bone to cause the bone to be cut.

14. The bone cutter of claim 13 wherein the first blade cutting portion resides distal of the second blade cutting portion and the second blade cutting portion resides distal of the third blade cutting portion.

15. The bone cutter of claim 13 wherein the first cutting blade comprises a first rake angle that extends between a first imaginary line that resides substantially through a middle of a thickness of the first blade engagement portion extending parallel to the longitudinal axis and a second imaginary line that is coincident with a first blade side edge, the first blade side edge positioned perpendicular to the first cutting edge.

16. The bone cutter of claim 13 wherein the second cutting blade comprises a second rake angle that extends between a first imaginary line that resides substantially through a middle of a thickness of the second blade engagement portion extending parallel to the longitudinal axis and a second imaginary line that lies coincident with a second blade side edge, the second blade side edge formed at an intersection of a distal end of a first sidewall surface and a third sidewall surface, the first and third sidewall surfaces oriented perpendicular to each other.

17. The bone cutter of claim 13 wherein the second cutting blade comprises a chamfer angle that extends between a third imaginary line that lies coincident with the second cutting edge and a fourth imaginary line that is positioned perpendicular to the longitudinal axis and extends through an imaginary point wherein the second cutting edge and a second blade side edge meet, the second blade side edge formed at an intersection of a distal end of a first sidewall surface and a third sidewall surface, the first and third sidewall surfaces oriented perpendicular to each other.

18. The bone cutter of claim 13 wherein the third cutting blade comprises a third rake angle that extends between a first imaginary line that resides substantially through a middle of a thickness of the third blade engagement portion extending parallel to the longitudinal axis and a second imaginary line that is coincident with a third blade side edge positioned perpendicular to the third cutting edge.

19. The bone cutter of claim 13 wherein an opening extends along the longitudinal axis through a thickness of the first base of the first housing portion, wherein the opening provides a space for at least a portion of the second housing portion to extend therethrough.

20. A bone cutter, comprising:
   a) a housing that extends along a longitudinal axis, the housing comprising an annular sidewall that extends from a base at a housing proximal end, wherein a first slot extends at least partially through the first housing portion annular sidewall, and wherein a second slot extends at least partially through a thickness of the housing base;
   b) a first cutting blade having a first blade engagement portion extending to a first blade cutting portion with a first blade cutting edge, wherein the first blade engagement portion is received within the first slot;
   c) a second cutting blade comprising a second blade sidewall extending from a second blade engagement portion to a second blade cutting portion, the second blade engagement portion received within the second slot, wherein the second blade sidewall comprises opposed first and second sidewall surfaces, a second cutting blade thickness therebetween, and opposed third and fourth sidewall surfaces oriented perpendicular to the opposed first and second sidewall surfaces, wherein a second cutting edge is formed where a distal end of the first sidewall surface and a distal end sidewall surface meet, the distal end sidewall surface residing between distal ends of the opposed first and second sidewall surfaces, and wherein the second cutting blade comprises a chamfer angle that extends between a first imaginary line coincident with the second cutting edge and a second imaginary line positioned perpendicular to the longitudinal axis and that extends through an imaginary point wherein the second cutting edge and the third sidewall surface meet; and
   d) wherein the bone cutter is configured to be rotated against a bone to cause the bone to be cut by the first and second cutting blades.

21. The bone cutter of claim 20 wherein the first blade cutting portion resides distal of the second blade cutting portion.

22. The bone cutter of claim 20 wherein the first cutting edge of the first blade cutting portion is oriented perpendicular to the longitudinal axis.

23. The bone cutter of claim 20 wherein the first cutting blade comprises a first rake angle that extends between a third imaginary line that resides substantially through a middle of a thickness of the first blade engagement portion extending parallel to the longitudinal axis and a fourth imaginary line that is coincident with a first blade side edge oriented perpendicular to the first cutting edge.

24. The bone cutter of claim 20 wherein the second cutting blade comprises a second rake angle that extends between a third imaginary line that resides substantially through a middle of the second cutting blade thickness of the second blade engagement portion and a fourth imaginary line that lies coincident with a second blade side edge, the second blade side edge formed at an intersection of a distal end of the first sidewall surface and the third sidewall surface.

25. The bone cutter of claim 20 wherein a shaft having opposed proximal and distal shaft ends is joined to the housing base, the shaft distal end contacting the housing proximal end.

26. The bone cutter of claim 25 wherein an inlet extends within a thickness of the shaft through the shaft distal end to a point distal of the shaft proximal end.

* * * * *